(12) United States Patent
Izumori et al.

(10) Patent No.: US 7,205,141 B2
(45) Date of Patent: Apr. 17, 2007

(54) GENE SEQUENCE OF L-RHAMNOSE ISOMERASE HAVING NEW CATALYTIC FUNCTION AND USE THEREOF

(75) Inventors: Ken Izumori, Takamatsu (JP); Goro Takada, Takamatsu (JP); Masaaki Tokuda, Takamatsu (JP)

(73) Assignee: National University Corporation Kagawa University, Takamatsu-shi, Kagawa (JP)

( * ) Notice: Subject to any disclaimer, the term of this patent is extended or adjusted under 35 U.S.C. 154(b) by 0 days.

(21) Appl. No.: 10/541,822

(22) PCT Filed: Jan. 9, 2004

(86) PCT No.: PCT/JP2004/000131

§ 371 (c)(1),
(2), (4) Date: Feb. 13, 2006

(87) PCT Pub. No.: WO2004/063369

PCT Pub. Date: Jul. 29, 2004

(65) Prior Publication Data

US 2006/0148061 A1    Jul. 6, 2006

(30) Foreign Application Priority Data

Jan. 10, 2003 (JP) ............................. 2003-005041
Mar. 31, 2003 (JP) ............................. 2003-096046
Aug. 22, 2003 (JP) ............................. 2003-299371

(51) Int. Cl.
*C07H 21/04* (2006.01)
*C12P 21/06* (2006.01)
*C12N 9/90* (2006.01)
*C12N 1/21* (2006.01)

(52) U.S. Cl. .................... 435/233; 435/105; 435/69.1; 435/252.34; 435/471; 536/23.2

(58) Field of Classification Search ..................... None
See application file for complete search history.

(56) References Cited

FOREIGN PATENT DOCUMENTS

| EP | 0560284 B1 | 7/1997 |
|---|---|---|
| JP | 57-129671 | 8/1982 |
| JP | 2286620 | 11/1990 |
| JP | 4198115 | 7/1992 |
| JP | 5112455 | 5/1993 |
| JP | 7285871 | 10/1995 |
| JP | 2000103728 | 4/2000 |

OTHER PUBLICATIONS

Korndorfer et al. J. Molecul. Biol. 2000, 300, 917-933).*
Bhuiyan, S.H., et al., "Preparation of L-Talose and D-Gulose from L-Tagatose and D-Sorbose, Respectively, Using Immobilized L-Phamnose Isomerase", Journal of Bioscience and Bioengineering, vol. 88, No. 5, p. 567-570, 1999.
Bhuiyan, S.H., et al., "Immobilization of L-Rhamnose Isomerase and Its Application in L-Mannose Production from L-Fructose", Journal of Fermentation and Bioengineering, vol. 84, No. 6, p. 558-562, 1997.
Bhuiyan, S.H., et al., "D-Allose Production from D-Psicose Using Immobilized L-Rhamnose Isomerase", Journal of Fermentation and Bioengineering, vol. 85, No. 5, p. 539-541, 1998.
Bhuiyan, S.H., et al., "Isolation of an L-Rhamnose Isomerase-Constitutive Mutant of Pseudomonas sp. Strain LL172: Purification and Characterization of the Enzyme" Journal Fermentation and Bioengineering, vol. 84, No. 4, p. 319-323, 1997.
Shigeru Mio et al, "Synthetic Studies on (+) −Hydantocidin (3): A New Synthetic Method for Construction of the Spiro-Hydantoin Ring at the Anomeric Position of D-Ribofuranose", Tetrahedron vol. 47, No. 12/13, p. 2133-2144, 1991.
Annie Grouiller et al. "Synthesis of D-Psico-and D-Fructofuranosyl Nucleosides", Acta Chemica Scandinavica B., vol. 38, No. 5, p. 367-373, 1984.

* cited by examiner

*Primary Examiner*—Rebecca E. Prouty
*Assistant Examiner*—Md Younus Meah
(74) *Attorney, Agent, or Firm*—Westerman, Hattori Daniels & Adrian LLP

(57) ABSTRACT

In the rare sugar strategy of Izumoring (FIG. 1), it is intended to establish a reaction system of producing rare sugars of many types by acquiring an isomerase which acts on various rare aldoses and, therefore, is most efficient in producing various rare ketoses. A DNA encoding the following protein (a) or (b). The above-mentioned DNA which is L-rhamnose isomerase derived from *Pseudomonas stutzerii*. A protein comprising the amino acid sequence represented by SEQ ID NO:2. A process for producing a recombinant protein characterized by culturing a host cell containing an expression system that can express the above-mentioned protein in a medium and collecting a recombinant protein having an L-rhamnose isomerase activity from the thus obtained culture. A method of applying FIG. 1 to the production of a rare sugar characterized in that the location of a target rare sugar in the overall picture of monosaccharides is understood and thus the optimum production pathway on which the above protein is allowed to act is designed.

3 Claims, 10 Drawing Sheets

Fig. 1

| | | |
|---|---|---|
| Aldotetrose (4) | DEry | D-Erythrose |
| | DThr | D-Threose |
| | LEry | L-Erythrose |
| | LThr | L-Threose |
| Ketotetrose (2) | DEry | D-Erythrulose |
| | LEry | L-Erythrulose |
| Tetritol (3) | D,LEry | D-,L-Erythitol |
| | DThr | D-Threitol |
| | LThr | L-Threitol |
| (Tetroses 9) | | |
| Aldopentose (8) | DRib | D-Ribose |
| | DAra | D-Arabinose |
| | DXyl | D-Xylose |
| | DLyx | D-Lyxose |
| | LRib | L-Ribose |
| | LAra | L-Arabinose |
| | LXyl | L-Xylose |
| | LLyx | L-Lyxose |
| Ketopentose (4) | DRib | D-Ribulose |
| | DXyl | D-Xylulose |
| | LRib | L-Ribulose |
| | LXy | L-Xylulose |
| Pentitol (4) | D,LRib | D-Ribitol,L-Ribitol |
| | DAra | D-Arabitol |
| | D,LXyl | D-Xylitol,L-Xylitol |
| | LAra | L-Arabitol |
| (Pentoses 16) | | |
| Aldohexose (16) | DAll | D-Allose |
| | DAlt | D-Altrose |
| | DGlu | D-Glucose |
| | DMan | D-Mannose |
| | DGul | D-Gulose |
| | DIdo | D-Idose |
| | DGal | D-Galactose |
| | DTal | D-Talose |
| | LAll | L-Allose |
| | LAlt | L-Altrose |
| | Lglu | L-Glucose |
| | DMan | L-Mannose |
| | LGul | L-Gulose |
| | LIdo | L-Idose |
| | LGal | L-Galactose |
| | LTal | L-Talose |
| Ketohexose (8) | DFru | D-Fructose |
| | DPsi | D-Psicose |
| | DSor | D-Sorbose |
| | DTag | D-Tagatose |
| | LFru | L-Fructose |
| | LPsi | L-Psicose |
| | LSor | L-Sorbose |
| | LTag | L-Tagatose |
| Hexitol (10) | D,LAll | D-Allitol,L-Allitol |
| | DAlt,DTal | D-Altritol,D-Talitol |
| | DGlu,LGul | D-Glucitol,L-Gulitol |
| | DMan | D-Mannitol |
| | DGul,LGlu | D-Gulitol,L-Glucitol |
| | DIdi | D-Iditol |
| | D,LGal | D-Galactitol,L-Galactitol |
| | LAlt,LTal | L-Altritol,L-Talitol |
| | LMan | L-Mannitol |
| | LIdi | L-Iditol |
| (Hexoses 34) | | |

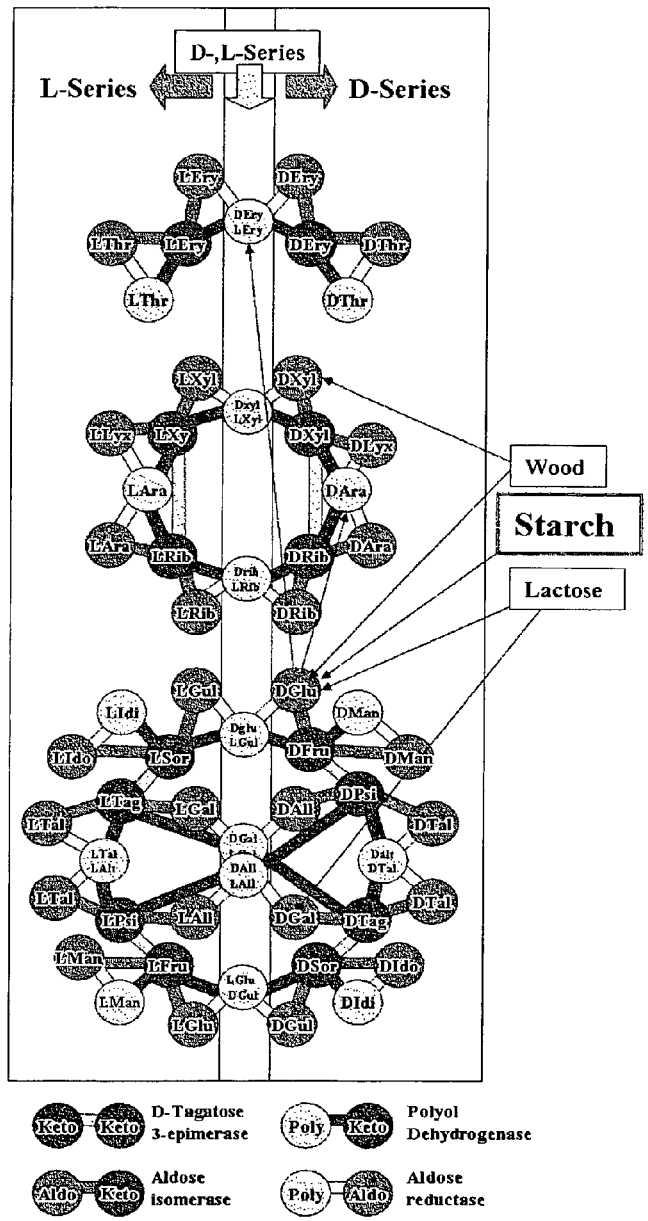

Biosynthesis strategy for all monosaccharides using Izumoring

Fig. 2

```
   1  ATGGCTGAATTCAGGATCGCTCAGGATGTCGTTGCGCGGGAAAACGACAGGCGCGCCTCG   60
   1  M  A  E  F  R  I  A  Q  D  V  V  A  R  E  N  D  R  R  A  S    20
  61  GCGCTGAAGGAAGACTACGAGGCGCTCGGCGCGAATCTCGCCCGCCGTGGCCGTCGACATC  120
  21  A  L  K  E  D  Y  E  A  L  G  A  N  L  A  R  R  G  V  D  I    40
 121  GAGGCCGTCACGGCCAAGGTCGAAAAGTTCTTCGTCGCCGTCCCCTCCTGGGGCGTCGGC  180
  41  E  A  V  T  A  K  V  E  K  F  F  V  A  V  P  S  W  G  V  G    60
 181  ACGGGCGGCACGCGCTTTGCGCGCTTCCCCGGCACCGGCGAGCCGCGCGGCATCTTCGAC  240
  61  T  G  G  T  R  F  A  R  F  P  G  T  G  E  P  R  G  I  F  D    80
 241  AAGCTGGACGACTGCGCCGTCATCCAGCAGCTGACACGCGCCACGCCCAATGTCTCGCTG  300
  81  K  L  D  D  C  A  V  I  Q  Q  L  T  R  A  T  P  N  V  S  L   100
 301  CATATTCCGTGGGACAAGGCCGATCCGAAGGAGCTGAAGGCCAGGGGCGACGCCCTCGGC  360
 101  H  I  P  W  D  K  A  D  P  K  E  L  K  A  R  G  D  A  L  G   120
 361  CTCGGCTTCGACGCGATGAACTCCAATACCTTCTCCGATGCGCCCGGCCAGGCGCATTCC  420
 121  L  G  F  D  A  M  N  S  N  T  F  S  D  A  P  G  Q  A  H  S   140
 421  TACAAATACGGCTCGCTCAGCCACACGGATGCGGCAACGCGCGCCCAGGCGGTCGAGCAC  480
 141  Y  K  Y  G  S  L  S  H  T  D  A  A  T  R  A  Q  A  V  E  H   160
 481  AATCTGGAATGCATCGAGATCGGCAAGGCCATCGGCTCCAAGGCGCTGACGGTCTGGATC  540
 161  N  L  E  C  I  E  I  G  K  A  I  G  S  K  A  L  T  V  W  I   180
 541  GGTGACGGCTCCAACTTCCCCGGCCAGAGTAACTTCACCAGGGCTTTCGAACGTTATCTC  600
 181  G  D  G  S  N  F  P  G  Q  S  N  F  T  R  A  F  E  R  Y  L   200
 601  TCGGCGATGGCGGAGATCTACAAGGGCCTGCCGGATGACTGGAAGCTGTTCTCCGAGCAC  660
 201  S  A  M  A  E  I  Y  K  G  L  P  D  D  W  K  L  F  S  E  H   220
 661  AAGATGTACGAGCCGGCCTTCTATTCGACCGTCGTGCAGGACTGGGGCACGAATTATCTC  720
 221  K  M  Y  E  P  A  F  Y  S  T  V  V  Q  D  W  G  T  N  Y  L   240
 721  ATCGCCCAGACGCTCGGCCCCAAGGCCCAGTGCCTCGTCGATCTCGGCCATCACGCGCCG  780
 241  I  A  Q  T  L  G  P  K  A  Q  C  L  V  D  L  G  H  H  A  P   260
 781  AACACCAATATCGAGATGATCGTCGCCCGGCTCATCCAGTTCGGCAAGCTCGGCGGCTTC  840
 261  N  T  N  I  E  M  I  V  A  R  L  I  Q  F  G  K  L  G  G  F   280
 841  CATTTCAACGATTCCAAATACGGCGACGACGACCTCGATGCCGGCGCCATCGAGCCCTAT  900
 281  H  F  N  D  S  K  Y  G  D  D  D  L  D  A  G  A  I  E  P  Y   300
 901  CGCCTCTTCCTCGTCTTCAACGAGCTGGTGGATGCGGAGGCGCGCGGCGTCAAGGGCTTC  960
 301  R  L  F  L  V  F  N  E  L  V  D  A  E  A  R  G  V  K  G  F   320
 961  CACCCGGCCCACATGATCGACCAGTCGCACAACGTCACCGACCCGATCGAGAGCCTGATC 1020
 321  H  P  A  H  M  I  D  Q  S  H  N  V  T  D  P  I  E  S  L  I   340
1021  AACAGCGCGAACGAAATCCGTCGCGCCTATGCGCAGGCCCTCCTTGTCGACCGCGCGGCG 1080
 341  N  S  A  N  E  I  R  R  A  Y  A  Q  A  L  L  V  D  R  A  A   360
1081  CTTTCCGGCTACCAGGAGGACAACGACGCCCTGATGGCGACGGAAACGTTGAAGCGCGCC 1140
 361  L  S  G  Y  Q  E  D  N  D  A  L  M  A  T  E  T  L  K  R  A   380
1141  TACCGTACCGATGTGGAGCCGATCCTCGCCGAGGCCCGCCGCCGCACGGGCGGCGCCGTC 1200
 381  Y  R  T  D  V  E  P  I  L  A  E  A  R  R  R  T  G  G  A  V   400
1201  GACCCCGTCGCGACCTATCGGGCCAGCGGCTACCGCGCCAGGGTCGCCGCCGAGCGCCCC 1260
 401  D  P  V  A  T  Y  R  A  S  G  Y  R  A  R  V  A  A  E  R  P   420
1261  GCCTCCGTCGCGGGTGGCGGCGGCATCATCTGA 1293
 421  A  S  V  A  G  G  G  G  I  I  *   431
```

Fig. 3

```
M---AEFRIAQDVVARENDRRASALKEDYEALGANLARRGVDIEAVTAKVEKFFVA--VP    55
MTIKANYDSAKQAYEKWGIDVEEALRQLEQVPISIHCWQGDDIEGFEVNKGELSGGIDVT   60

SWGVGTGGTRFARFPGTGEPRGIFDKLDDCAVIQQLTRATPNVSLHIPWDKADPKELKAR  115
GNYPGKAQTPEELRRDLEKALSLIPGKHRVNLHAIYAETNREAVERDELKPQHFENWVKW  120

GDALGLGFDAMNSNTFSDAPGQAHSYKYGSLSHTDAATRAQAVEHNLECIEIGKAIGSKA  175
AKNLGLGLDFNPTLFSHEKAADGLT-----LSHPDPDIREFWIRHCIACRRIGEYFGKEL  175

LTVWIGDGSNFPGQSNFTR----AFERYLSAMAEIY-KGLPDDWKLFS-EHKMYEPAFYS  229
GTPCLTNIWIPDGYKDIPSDRLTPRKRLKESLDRIFSEEISEQHNLDSIESKLFGLGSES  235

TVVQDWGTNYLIAQTLGPKAQCLVDLGH-HAPNTNIEMIVARLIQFGKLGGFHFNDSKYG  288
YVV--GSHEFYLAYALTNHKLCLLDTGHFHPTETVSNKISSMLLYTDKLA-LHVSRPVRW  292

DDDLDAGAIEPYRLFLVFNELVDAEARGVKGFHPAHMIDQSHNVTDPIESLINSANEIRR  348
DSDHVVVLDDELR------EIALEIVRNHALEKVAIGLDFFDASINRVAAWTIGTRNMIK  346

AYAQALLVDRAALSGYQEDNDALMATETLKRAYRTDVEPILAEARRRTGGAVDPVATYRA  408
ALLYALLLPNGYLKQLQEEGRYTERLALMEEFKTYPFGAIWDSYCEQMQVPVKEAWLYDI  406

SGYRARVAAERPASVAGGGGII   430
KEYEQQVLLKRKASSP----IV  424
```

上: *Pseudomonas stutzeri*
下: *Bacillus subtilis*

Fig. 4

```
Rhl    MAEFRIAQDVVARENDRRASALKEDYEALGANLARRGVDIEAVTAKVEKFFVAVPSWGVG    60
SISTR  MTE---------------------------------LAAVKAALKTQAVETPSWAYG     24
SITHE  MI----------------------------------NMERIFKELDELKFELPSWAFS    24

Rhl    TGGTRFARFPGTGEPRGIFDKLDDCAVIQQLTRATPNVSLHIPWDKA-DPKELKARGDAL   119
SISTR  NSGTRFKVFAQPGVPRDPFEKLDDAAKVHEFTGAAPTVALHIPWDRVEDYAALAAHAEKR   84
SITHE  DAGTRFAVFHEEGAARNVFERIEDAALVHRLTGCCPSVALHIPWDKVENWEELREFAEEK   84

Rhl    GLGFDAMNSNTFSDAPGQAHSYKYGSLSHTDAATRAQAVEHNLECIEIGKAIGSKALTVW   179
SISTR  GVRIGAINSNTFQDD----DYRLGSICHPDAAVRRKAVDHLLECVDIMDATGSRDLKLW   139
SITHE  GLKIGAINPNLFQDP----DYKYGSLTNPSEKIRKKAIAHVMECVDIAEKTGSKVISLW   139

Rhl    IGDGSNFPGQSNFTRAFERYLSAMAEIYKGLPDDWKLFSEHKMYEPAFYSTVVQDWGTNY   239
SISTR  FADGTNYPGQDDIRSRQDRLAEGLAEVYERLGEGQRMLLEYKLFEPAFYTTDVPDWGTAY   199
SITHE  LADGTDYPGQDDFRSRKKRLEESLRYIYENMPADMYLLIEYKFFEPAFYHTDIPDWGMSY   199

Rhl    LIAQTLGPKAQCLVDLGHHAPNTNIEMIVARLIQFGKLGGFHFNDSKYGDDDLDAGAIEP   299
SISTR  AHCLKLGEKAQVVVDTGHHAPGTNIEFIVATLLREGKLGGFDFNSRFYADDDLMVGAADP   259
SITHE  LLSEKLGERALVLVDLGHHPQGTNIEYIVATLLSEKKLGGFHLNNRKYADDDLTIASINP   259

Rhl    YRLELVFNELVDAEARGVKGFH--PAHMIDQSHNVTDPIESLINSANEIRRAYAQALLV   356
SISTR  FQLERI--MYEVVRGGGFTSD--VAFMLDQCHNIEAKIPAIIRSVMNVQEATAKALLV   313
SITHE  YEVELIFKEIVFAKRDPELSDSAKKVVLMFDQAHITKPKILAMIQSVLIAQELFTKALLI   319

Rhl    DRAALSGYGEDNDALMATETLKRAYRTDVEPILAEARRRTGGAVDPVATYRASGYRARVA   416
SISTR  DGTALAEAQAAGDVLEANAVLMDAYNTDVRPLLREVREESGLDPEPMKAYRSCGWAEKVV   373
SITHE  DENRLREAQKNYDVVEAEEILLDAFRTDVRPILREYRRQKGLPEDPLRVFREEDYMEKRR   379

Rhl    AERPASVAGGGGII    430
SISTR  AERIGGQQAGWG-A   386
SITHE  RERR---------    383
```

GENE SEQUENCE OF L-RHAMNOSE ISOMERASE HAVING NEW CATALYTIC FUNCTION AND USE THEREOF

TECHNICAL FIELD

The present invention reveals that a gene sequence encoding L-rhamnose isomerase produced by *Pseudomonas stutzeri* and further a new catalytic function catalyzing an isomerization reaction of a sugar, which had not been found so far, and relates to a the novel gene sequence, the novel catalytic function and application of the novel catalytic function to the production of a rare sugar and the search for its physiological activity.

In the present invention, correlation diagrams of Izumoring to be utilized are the linkage in Izumoring C6 (FIG. 5, Japanese Trademark Application No. 2003-1630), the linkage in Izumoring C5 (FIG. 6, Japanese Trademark Application No. 2003-1631), the linkage in Izumoring C4, and the overall diagram of Izumoring shown in FIG. 1 in which C4, C5 and C6 are all linked together, which had not been published before filing an application.

In addition, L-rhamnose isomerase was isolated from a variety of microorganisms and the gene sequence encoding it has been also reported. In the present invention, when the gene sequence encoding L-rhamnose isomerase from a bacterium (*Pseudomonas stutzeri*) isolated from the soil was determined, it was found that the gene sequence does not have homology with the gene sequences which had been reported so far, and it is a novel gene on a gene basis as well as a protein basis.

By utilizing this sequence, an enzyme is produced in a large amount by using genetic engineering and the production of a rare sugar can be carried out using the produced enzyme, or this sequence can be applied to the use using a variety of genetic engineering techniques other than this.

Still further, the present invention reveals that L-rhamnose isomerase produced by *Pseudomonas stutzeri* has a new catalytic function catalyzing an isomerization reaction of a sugar, which had not been found so far.

L-rhamnose isomerase is a useful enzyme in the production of a rare sugar, D-allose, from D-psicose. In the present invention, a pure enzyme was produced and investigated using a genetic engineering technique, and as a result, a new ability of catalyzing an isomerization reaction, which had not been identified so far, was found, which can be applied to the production of a variety of rare sugars.

BACKGROUND ART

With regard to a conventional effective utilization of unused resources, particularly biomass (e.g., wood waste material and the like), a major goal was to hydrolyze it into glucose and to convert the glucose into an alcohol. However, even if it was converted into an alcohol, since its added value is low, it was unreasonable to put it into practical use. In addition, by using a polysaccharide (which exists unlimitedly in unused resources) as a raw material, when it is incompletely degraded, an oligosaccharide can be produced. Its application is also being developed as a value-added product having a functionality.

The present inventors started focusing on the physiological activity of rare sugars and confirming it by experiments using cells. 21 century is also called a century of life science, and at present, a DNA study and a protein study are being advanced internationally. Speaking of sugar in post-genomic study, the study is centered on sugar chains, however, in Kagawa Medical University (at present, the Faculty of Medicine in Kagawa University) and the Faculty of Agriculture in Kagawa University to which the present inventors belong, monosaccharides are focused on and their application study such as whether or not the monosaccharides have a physiological activity has been advanced. The background includes the fact that in the Faculty of Agriculture in Kagawa University, a long series of exhaustive studies on the production of rare sugars has been continued for a long time, and recently, a technique of the mass production of part of rare sugars was established. In also Kagawa Medical University (at present, the Faculty of Medicine in Kagawa University), a study of searching for a physiological activity in sugars was started several years ago. A study of searching for a physiological activity by using rare sugars (monosaccharides) produced in the Faculty of Agriculture in Kagawa University was started from 1999 as a regional leading study in a manner that both studies were put together, and it was found that they have various physiological activities.

Monosaccharides are classified broadly into aldoses (sugars having an aldehyde group as a carbonyl group), ketoses (sugars having a ketone group as a carbonyl group) and sugar alcohols (another name: polyols, sugars without a carbonyl group) based on the state of a reducing group (carbonyl group). There is a monosaccharide called "rare sugar". A rare sugar is defined as a sugar that rarely exists in nature according to the definition of International Society of Rare Sugars. There are many types of rare sugars whose yield is small by an organic chemical synthetic method depending on the type. Accordingly, the present situation is that there are also many types of rare sugars whose property is not known, and that there are many unknown properties for aldohexose (aldose) rare sugars including allose.

In application studies of sugars, conventionally, with regard to the correlation between a sugar and cancer, for example, as described in Patent Document 1, a polysaccharide that is effective in prevention of cancer is known. In addition, there are reports that an oligosaccharide has an effect on counteracting constipation by utilizing the fact that it has an action of regulating the intestines thereby to cause less colon cancer, and recently that a polysaccharide such as agaricus has an effect on suppressing cancer, and also a report on the correlation between a sugar chain and cancer metastasis. Further, in Patent Document 2, an anti-tumor agent containing a derivative of D-allose as the active ingredient is disclosed. On the other hand, as for utilizing a property of a saccharide against active oxygen, for example, as described in Patent Document 3, an inhibitor of active oxygen production containing a polysaccharide having a property of inhibiting active oxygen is known.

Among monosaccharides, psicose is a hexose having a ketone group as a reducing group. It is known that psicose exists as optical isomers in D-form and L-form. Here, although D-psicose is a known substance, it rarely exists in nature, therefore, it is defined as a "rare sugar" according to the definition of International Society of Rare Sugars. However, it became relatively easy to obtain this D-psicose recently, though it is expensive, because of the emergence of epimerase (e.g., see Patent Document 4). According to this official gazette, it is suggested that the prepared D-psicose can be effectively utilized as a sweetener, a carbon source for fermentation, a reagent, a raw material or an intermediate for a cosmetic or a medical product or the like. According to this official gazette, as the sweetener, it only describes a direction of application that it can be utilized in improving the taste for sweetening an oral intake item such as food and drink, feed, toothpaste or a medicine for internal use. With regard to L-psicose that is an optical isomer of D-psicose, the fact that it can be utilized as an edible composition is disclosed in, for example, Patent Document 5 in detail.

On the other hand, an example of application of psicose as an intermediate material for a reagent, a medical product or the like is shown below. For example, according to Non-Patent Document 1, an example of synthesis of a hydantoin derivative using D-psicose as a raw material is reported. In addition, according to Non-Patent Document 2, an example of synthesis of D-fructofranosyl nucleoside is disclosed. In any prior art, it is only reported that D-psicose can be utilized as a raw material or an intermediate for a medical product or the like.

In addition, in Patent Document 6, it is only described that a kojic acid glycoside having a hexose in its structure is excellent in an action of inhibiting melanogenesis, high in stability, high in solubility in water and suitable as the active ingredient of a whitening preparation for external use. In addition, in Patent Document 7, it is described that psicose promotes recovery of the skin barrier function and is useful in preventing such as abnormality of the epidermal growth due to a decrease in the epidermal function of the skin, and the usefulness as a humectant is only described. In addition, a healthy diet for prevention of a disease accompanied by high blood glucose and prevention of obesity containing several saccharides including D-tagatose as an active ingredient is disclosed in Patent Document 8, however, the function of the rare sugar itself is not described. In addition, in Patent Document 9, the application, as an antihyperlipidemic agent, of a polysaccharides complex containing, as the major constituent sugars, arabinose, ribose and glucose including D-sorbose which is one of ketohexoses is only published.

However, in order to advance the study of application of a rare sugar by focusing on a "monosaccharide", and moreover, in the case where a new application has been completed, it is necessary to establish a technique of mass production of a rare sugar.

On the other hand, L-rhamnose isomerase produced by *Pseudomonas stutzerii* LL172 is a known enzyme having the following physicochemical properties published in Non-Patent Document 3.

(i) Action

It is an enzyme catalyzing an isomerization reaction from L-rhamnose to L-rhamnulose and isomerization from L-rhamnulose to L-rhamnose. It is known that it also acts on isomerization between D-allose and D-psicose (Non-Patent Document 3), and it is an enzyme that can produce D-allose from D-psicose. Isomerases are named based on a substrate exhibiting the highest activity, therefore, an enzyme named the same L-rhamnose isomerase were isolated from *E. coli* and *Bacillus subtilis*, and the gene sequence encoding it has been reported.

(ii) Substrate Specificity

L-rhamnose and L-rhamnulose are used as a substrate. Other than these, L-lyxose and L-xylulose, L-mannose and L-fructose, D-ribose and D-ribulose, D-allose and D-psicose are used as a substrate.

(iii) Active pH and Optimal pH

The active pH ranges from 7.0 to 10.0 and the optimal pH is 9.0.

(iv) pH Stability

It is stable within the pH range of 6.0 to 11.0 in the case where it is kept at 4° C. for 1 hour at various pH values.

(v) Active Temperature and Optimal Temperature

The active temperature ranges from 40 to 65° C. and the optimal temperature is 60° C.

(vi) Temperature Stability

It is stable at 40° C. for 10 minutes and remains at 90% or more even at 50° C. for 10 minutes.

(vii) Effect of a Chelating Agent

Its activity is hardly inhibited even if it coexists with EDTA or EGTA, which is a chelating agent, during the measurement of its activity.

(viii) Effect of a Metal Ion

About 30% of the activity is inhibited by 1 mM cobalt ion.

(ix) Molecular Weight by the SDS-PAGE Method

It is about 43,000.

Patent Document 1: JP-A-5-112455
Patent Document 2: JP-B-59-40400
Patent Document 3: JP-A-07-285871
Patent Document 4: JP-A-6-125776
Patent Document 5: JP-A-57-129671
Patent Document 6: JP-A-4-198115
Patent Document 7: JP-A-2000-103728
Patent Document 8: JP-A-6-65080
Patent Document 9: JP-A-2-286620
Non-Patent Document 1: Tetrahedron Vol. 47, No. 12/13, pp.2133 (1991)
Non-Patent Document 2: Acta. Chem. Scand. Ser. B. Vol. 38, No. 5, pp. 367 (1984)
Non-Patent Document 3: "Journal of Fermentation and Bioengineering", Vol. 85, pp. 539 to 541 (1998)

DISCLOSURE OF THE INVENTION

With regard to a process for producing each rare sugar, a plan diagram in which each rare sugar can be produced by Izumoring strategy for producing rare sugars (correlation diagram in which all the monosaccharides having different number of carbon atoms are linked together based on their production processes and molecular structures (D-form and L-form) shown in FIG. 1) has been completed by the present inventors. An isomerase catalyzing the reaction between an aldose and a ketose in the strategy is important for producing a rare aldose and a rare ketose. In general, an aldose isomerase has a relatively broad substrate specificity. More specifically, for example, D-xylose isomerase catalyzed isomerization between D-xylose and D-xylulose, however, it also catalyzes isomerization between D-glucose and D-fructose as well as this reaction. Though it has a broad substrate specificity, aldoses to be a substrate are generally 3 to 4 types. D-arabinose isomerase acts on the ones having a relatively similar structure as it acts on D-arabinose, L-galactose, L-fucose and the like.

Accordingly, in the production of various rare aldoses and rare ketoses in Izumoring of FIG. 1, it becomes an important object for investigation to produce a target rare sugar by performing investigation in view of its structure.

An object of the present invention is to apply Izumoring in FIG. 1 (overall diagram of Izumoring) to production of a rare sugar.

The present invention is the same as conventional methods up to the point where a polysaccharide (which exists unlimitedly in unused resources) is used as a raw material and it is converted into a monosaccharide such as glucose. An object of the present invention is to design the optimum production pathway to a rare sugar which has a high added value instead of alcohol fermentation by yeast after the conversion into a monosaccharide, and to establish a technique of mass production of a rare sugar.

An object of the present invention is to provide a gene sequence encoding L-rhamnose isomerase produced by *Pseudomonas stutzeri*, to find a new catalytic function catalyzing an isomerization reaction of a sugar, which had not been found so far, by a variety of genetic engineering techniques and to apply the novel catalytic function to the production of a rare sugar and the search for its physiological activity.

An object of the present invention is to provide a novel and useful L-rhamnose isomerase gene sequence, and to enable to apply the gene sequence to the production of a rare sugar by utilizing genetic engineering and also the found novel catalytic function, to a variety of genetic engineering techniques, or to the use using the novel catalytic function.

An object of the present invention is to apply a gene sequence encoding L-rhamnose isomerase produced by *Pseudomonas stutzeri* and also the found novel catalytic function to the production of a rare sugar by using the overall diagram of Izumoring, and further to contribute to the search for a physiological activity of a rare sugar.

Further, an object of the present invention is to establish a reaction system for producing many types of rare sugars by obtaining an isomerase which acts on many types of rare aldoses in the rare sugar strategy of Izumoring (FIG. 1) and is most efficient for producing many types of rare ketoses.

The present invention reveals a gene sequence encoding L-rhamnose isomerase produced by *Pseudomonas stutzerii*. L-rhamnose isomerase was isolated from a variety of microorganisms and the sequence of a gene encoding it has been also reported. However, there is no report that L-rhamnose isomerase derived from any of these produces D-allose by reacting with D-psicose.

In the present invention, when the sequence of a gene encoding L-rhamnose isomerase from a bacterium (*Pseudomonas stutzerii* LL172) isolated from the soil was determined, it was found that the gene sequence does not have homology with the gene sequences which had been reported so far, and it is a novel gene on a gene basis as well as a protein basis. By utilizing this sequence, an enzyme is produced in a large amount by using genetic engineering and the production of a rare sugar can be carried out using the produced enzyme, or this sequence can be applied to the use using a variety of genetic engineering techniques other than this.

It is resolved by providing a DNA-encoding L-rhamnose isomerase derived from *Pseudomonas stutzerii* catalyzing an isomerization reaction from L-rhamnose to L-rhamnulose and an isomerization reaction from L-rhamnulose to L-rhamnose, and a process for producing a polypeptide by a recombinant DNA technique using the DNA.

Further, the present inventors proceeded with the study and found that L-rhamnose isomerase produced by *Pseudomonas stutzeri* has a new catalytic function of catalyzing an isomerization reaction of sugar, which had not been found so far. In the present invention, a variety of rare sugars are produced by utilizing the catalytic ability that was newly discovered and is possessed by L-rhamnose isomerase, which is an enzyme catalyzing an isomerization reaction in the Izumoring (FIG. 1).

While conventionally, an individual isomerization reaction was carried out by using a different individual isomerase, by utilizing the extremely broad substrate specificity of L-rhamnose isomerase, it is intended to produce many types of rare sugars with the use of one enzyme.

More specifically, in the present invention, by allowing L-rhamnose isomerase to catalyze many isomerization reactions, it became possible to efficiently carry out the production of a variety of rare sugars by effectively applying one enzyme to the production of rare sugars, which had been impossible so far.

That is, a gist of the present invention is any of the following DNA.

(1) A DNA encoding the following protein (a) or (b):

(a) a protein comprising the amino acid sequence represented by SEQ ID NO:2;

(b) a protein comprising an amino acid sequence in which one or several amino acids have been deleted, replaced, or added in the amino acid sequence represented by SEQ ID NO: 2 and having an L-rhamnose isomerase activity.

(2) A DNA comprising the nucleotide sequence represented by SEQ ID NO: 1 or a complementary sequence thereof or a sequence containing a part or the whole of any of these sequences.

(3) A DNA hybridizing to the DNA described in the above-mentioned (2) under stringent conditions and encoding a protein having an L-rhamnose isomerase activity.

(4) The DNA described in the above-mentioned (1), (2) or (3), which is L-rhamnose isomerase derived from *Pseudomonas stutzerii*.

(5) The DNA described in the above-mentioned (4), in which the above-mentioned L-rhamnose isomerase is an enzyme having the following physicochemical properties:

(i) Action

It catalyzes an isomerization reaction represented by any of the bold black lines in FIG. 7, FIG. 8 and FIG. 9.

(ii) Active pH and Optimal pH

The active pH ranges from 7.0 to 10.0 and the optimal pH is 9.0.

(iii) pH Stability

It is stable within the pH range of 6.0 to 11.0 in the case where it is kept at 4° C. for 1 hour at various pH values.

(iv) Active Temperature and Optimal Temperature

The active temperature ranges from 40 to 65° C. and the optimal temperature is 60° C.

Temperature Stability

It is stable at 40° C. for 10 minutes and remains at 90% or more even at 50° C. for 10 minutes.

(vi) Effect of a Chelating Agent

Its activity is hardly inhibited even if it coexists with EDTA or EGTA, which is a chelating agent, during the measurement of its activity.

(vii) Effect of a Metal Ion

About 30% of the activity is inhibited by 1 mM cobalt ion.

(viii) Molecular Weight by the SDS-PAGE Method

It is about 43,000.

In addition, a gist of the present invention is any of the following proteins.

(6) A protein comprising the amino acid sequence represented by SEQ ID NO:2.

(7) A protein comprising an amino acid sequence in which one or several amino acids have been deleted, replaced, or added in the amino acid sequence represented by SEQ ID NO: 2 and having an L-rhamnose isomerase activity.

(8) The protein described in the above-mentioned (6) or (7), wherein the L-rhamnose isomerase activity is specified by the following physicochemical properties:

(i) Action

It catalyzes an isomerization reaction represented by any of the bold black lines in FIG. 7, FIG. 8 and FIG. 9.

(ii) Active pH and Optimal pH

The active pH ranges from 7.0 to 10.0 and the optimal pH is 9.0.

(iii) pH Stability

It is stable within the pH range of 6.0 to 11.0 in the case where it is kept at 4° C. for 1 hour at various pH values.

(iv) Active Temperature and Optimal Temperature

The active temperature ranges from 40 to 65° C. and the optimal temperature is 60° C.

(vi) Effect of a Chelating Agent (V) Temperature Stability

It is stable at 40° C. for 10 minutes and remains at 90% or more even at 50° C. for 10 minutes.

Its activity is hardly inhibited even if it coexists with EDTA or EGTA, which is a chelating agent, during the measurement of its activity.

(vii) Effect of a Metal Ion

About 30% of the activity is inhibited by 1 mM cobalt ion.

(viii) Molecular Weight by the SDS-PAGE Method

It is about 43,000.

(9) A fusion protein in which a protein described in the above-mentioned (6), (7) or (8) has been bound to a protein translation initiation codon.

In addition, a gist of the present invention is a recombinant vector described in the following (10).

(10) A recombinant vector containing a DNA described in any of the above-mentioned (1) to (5).

In addition, a gist of the present invention is a host cell described in the following (11).

(11) A host cell containing an expression system that can express a protein described in the above-mentioned (6), (7) or (8).

In addition, a gist of the present invention is a process for producing a recombinant protein described in the following (12).

(12) A process for producing a recombinant protein characterized by culturing a host cell described in the above-mentioned (11) in a medium and collecting a recombinant protein having an L-rhamnose isomerase activity from the thus obtained culture.

Still further, a gist of the present invention is a method of applying Izumoring correlation diagram to production of a rare sugar described in the following (13).

(13) A method of applying a correlation diagram in which all the monosaccharides having different number of carbon atoms are linked together based on their production processes and molecular structures (D-form and L-form) shown in FIG. 1 to production of a rare sugar characterized in that the location of a target rare sugar in the overall picture of monosaccharides is understood and thus its optimum production pathway on which a protein described in the above-mentioned (6), (7), (8) or (9) is allowed to act is designed.

(14) The method described in the above-mentioned (13), in which the production of a rare sugar is mass production of a rare sugar.

(15) The method described in the above-mentioned (13) or (14), in which the production of a rare sugar is production of a rare sugar from an unused resource.

(16) The method described in the above-mentioned (13), (14) or (15), in which the target rare sugar is a rare sugar whose physiological activity has been identified.

ADVANTAGE OF THE INVENTION

It becomes possible to produce L-rhamnose isomerase in a large amount by a genetic engineering technique, and a mass production method of a variety of rare sugars including D-allose using this enzyme can be established.

In the present invention, a raw material that can be obtained in a large amount at the lowest price is D-glucose (glucose). This D-glucose is a sugar existing in a large amount in almost all the unused plants. By effectively utilizing this sugar, a tool designing the optimum production pathway for a target rare sugar can be provided.

In addition, the present invention can provide an effective tool not only to a field for producing a rare sugar, but also to a study for searching for a physiological activity that a rare sugar possesses.

BRIEF DESCRIPTION OF THE DRAWINGS

FIG. 1 is a correlation diagram of Izumoring.

FIG. 2 is a figure showing the nucleotide sequence of a gene (DNA) encoding a protein having an L-rhamnose isomerase activity derived from *Pseudomonas stutzerii* LL172 of the present invention and the amino acid sequence.

FIG. 3 is a figure illustrating the comparison of the amino acid sequences of L-rhamnose isomerase derived from *Pseudomonas stutzerii* LL172 strain of the present invention and L-rhamnose isomerase derived from known *Bacillus subtilis*.

FIG. 4 is a figure illustrating the homology of L-rhamnose isomerase derived from *Pseudomonas stutzerii* LL172 strain of the present invention with an unidentified putative isomerase derived from known *Streptmyzes coelicolor* or *Thermotoga maritima*.

BEST MODE FOR CARRYING OUT THE INVENTION

Figure 5:
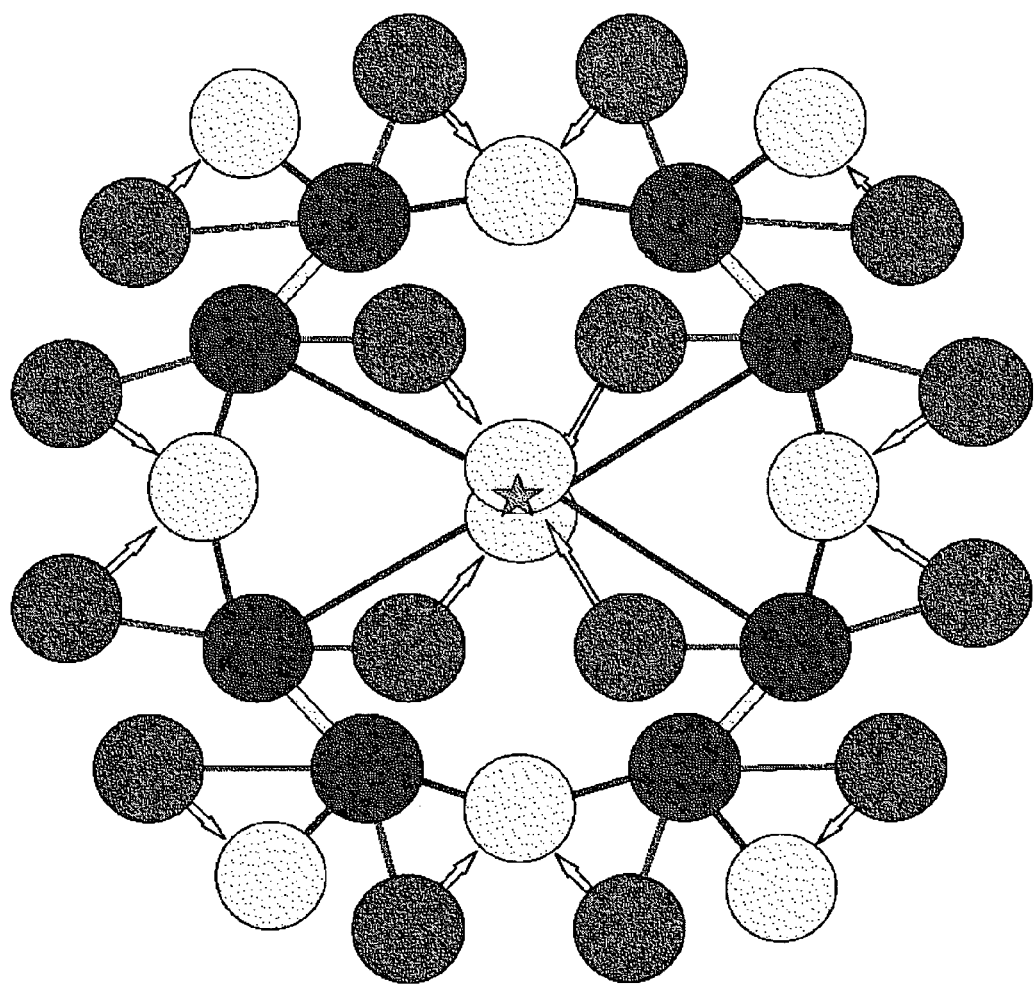
FIG. 5 is an illustration of Izumoring C6 at the lower portion of FIG. 1.

"*Pseudomonas stutzerii* LL172" strain belonging to the genus *Pseudomonas stutzerii* is a known bacterium described in the above-mentioned documents, and stored in the Ken Izumori Laboratory, Department of Biochemistry and Food Science, Faculty of Agriculture, Kagawa University. On the occasion of international application at this time, this strain was deposited at the International Patent Organism Depository, National Institute of Advanced Industrial Science and Technology (Central 6, 1-1-1 Higashi, Tsukuba, Ibaraki, Japan) on Jan. 6, 2004 (IPOD FERM BP-08593). Incidentally, this strain is sometimes represented by LL172a, however, LL172 and LL172a are the same strain.

L-rhamnose isomerase is an enzyme catalyzing an isomerization reaction from L-rhamnose to L-rhamnulose and isomerization from L-rhamnulose to L-rhamnose. L-rhamnose isomerase produced by *Pseudomonas stutzerii* LL172 also acts on isomerization between D-allose and D-psicose, therefore, it is an enzyme that can produce D-allose from D-psicose. However, in order to produce D-allose from D-psicose, an enzyme derived from *Pseudomonas stutzerii* LL172 is needed.

The gene sequence encoding L-rhamnose isomerase derived from *Pseudomonas stutzerii* LL172 does not have homology with the gene sequences encoding L-rhamnose isomerases which had been reported so far, and it is found to be a novel gene on a gene basis as well as a protein basis.

L-rhamnose isomerase according to the present invention is L-rhamnose isomerase derived from *Pseudomonas stutzerii* LL172, and has the amino acid sequence represented by SEQ ID NO:2 or an amino acid sequence in which one or more amino acids in the amino acid sequence have been replaced with another amino acid, deleted, or one or more amino acids have been added. The gene (DNA) according to the present invention has the nucleotide sequence encoding the above-mentioned L-rhamnose isomerase.

That is, as the protein to be a subject of the present invention, a protein comprising the amino acid sequence represented by SEQ ID NO:2 (L-rhamnose isomerase), and a protein comprising an amino acid sequence in which one or several amino acids have been deleted, replaced, or added in the amino acid sequence represented by SEQ ID NO:2 and having an L-rhamnose isomerase activity can be exemplified.

In addition, as the above-mentioned L-rhamnose isomerase activity, an enzymatic activity catalyzing an isomerization reaction from L-rhamnose to L-rhamnulose and isomerization from L-rhamnulose to L-rhamnose can be preferably exemplified. In addition, an enzymatic activity catalyzing isomerization between D-allose and D-psicose can be exemplified. There is no report on the activity that can produce D-allose from D-psicose other than L-rhamnose isomerase derived from *Pseudomonas stutzerii* LL172.

Further, it was revealed that L-rhamnose isomerase produced by *Pseudomonas stutzerii* LL172 is an enzyme having the following physicochemical properties.

(i) Action

It catalyzes an isomerization reaction from L-rhamnose to L-rhamnulose and isomerization from L-rhamnulose to L-rhamnose. It also acts on isomerization between D-allose and D-psicose, and it is an enzyme that can produce D-allose from D-psicose. These are major known actions. Further, all the isomerization reactions including novel catalytic reactions of L-rhamnose isomerase, which were found this time by the present inventors are shown in Izumorings of FIG. 7, FIG. 8 and FIG. 9. Refer to Tables 1, 2 and 3 for the substrate specificity.

L-rhamnose and L-rhamnulose are used as a substrate. Other than these, L-lyxose and L-xylulose, L-mannose and L-fructose, D-ribose and D-ribulose, D-allose and D-psicose are used as a substrate. These are major known substrate specificities. It can be understood that many types of monosaccharides are used as a substrate for L-rhamnose isomerase from FIG. 7, FIG. 8 and FIG. 9.

Figure 7:
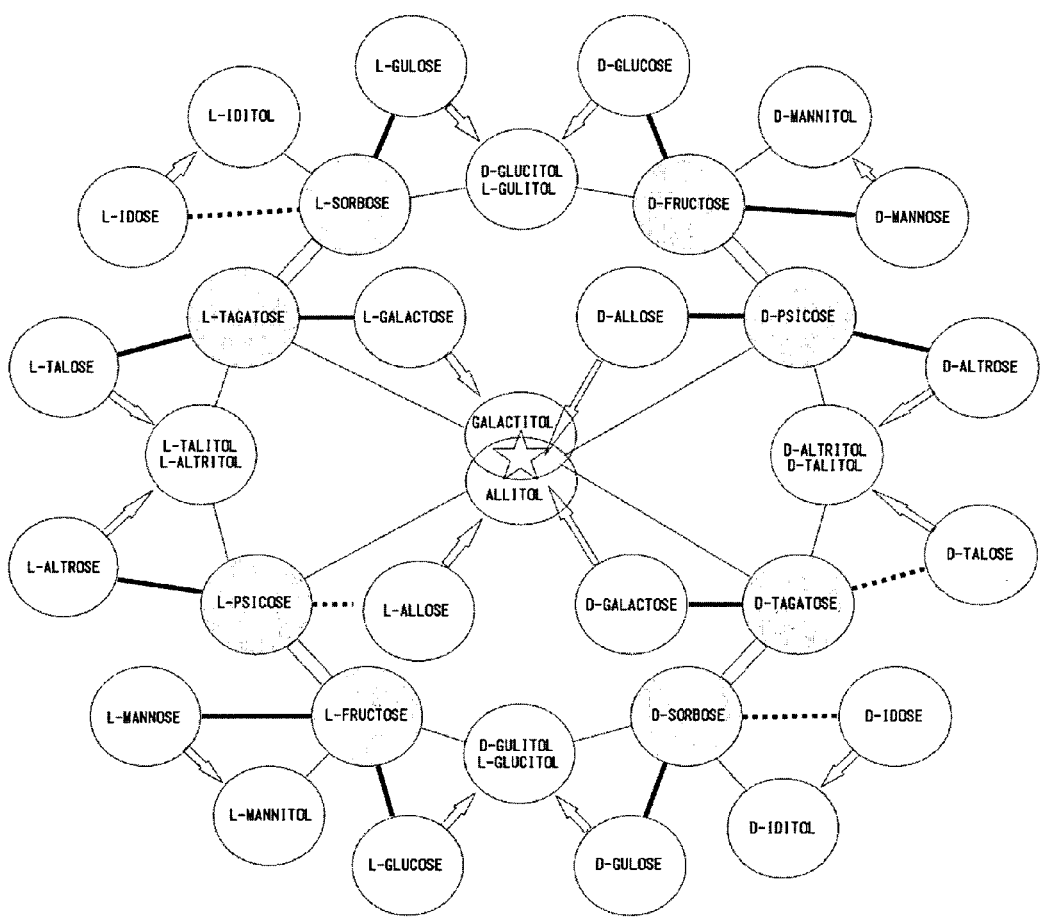
FIG. 7 shows isomerization reactions of hexoses catalyzed by L-rhamnose isomerase shown by using Izumoring. The bold black lines indicate the isomerization reactions which were confirmed to be catalyzed. The bold dotted lines indicate the isomerization reactions in which a catalytic reaction was not identified.

That is, though the activities vary in degree, the isomerization reactions which were confirmed to be catalyzed by L-rhamnose isomerase are represented by the bold black lines in FIG. 7. On the other hand, it can be plainly understood that there are 4 types of reactions represented by the bold dotted lines, in which the isomerization reaction could not be confirmed.

Figure 9:
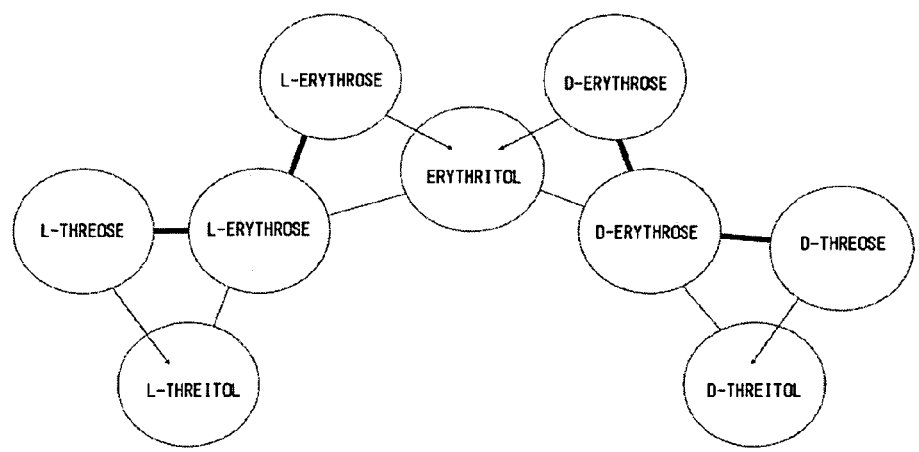
FIG. 9 shows isomerization reactions of hetetroses catalyzed by L-rhamnose isomerase shown by using Izumoring. The bold black lines indicate the isomerization reactions which were confirmed to be catalyzed. All the isomerization reactions were confirmed.
Figure 10:
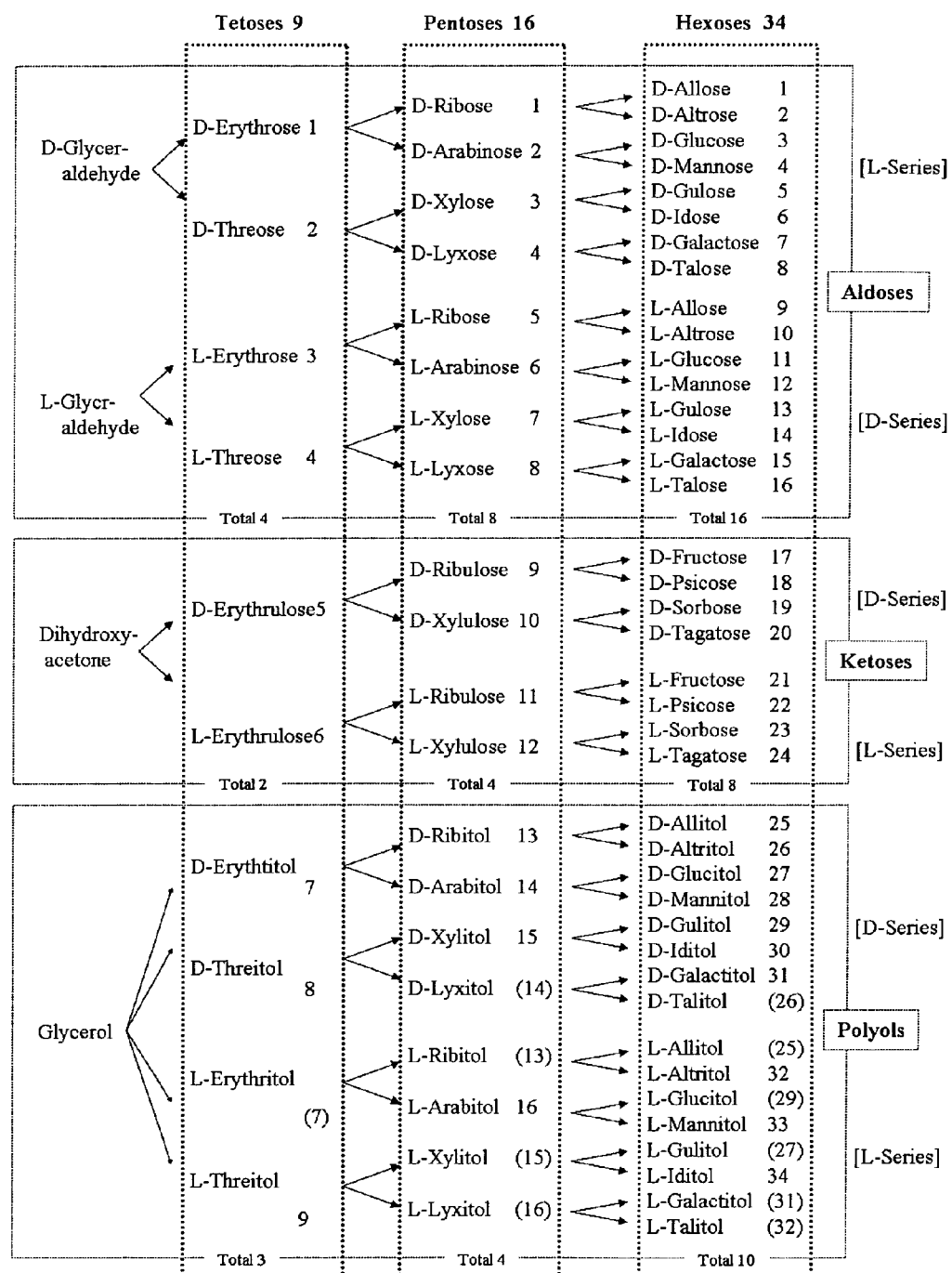
FIG. 10 is a diagram showing one example of the conventional ways of summarizing monosaccharides.

In addition, as shown in FIG. 9 and FIG. 10, though the activities also vary in degree, it is shown that it has all the isomerization activities for pentoses and tetroses.

(ii) Active pH and Optimal pH

The active pH ranges from 7.0 to 10.0 and the optimal pH is 9.0.

(iii) pH Stability

It is stable within the pH range of 6.0 to 11.0 in the case where it is kept at 40° C. for 1 hour at various pH values.

(iv) Active Temperature and Optimal Temperature

The active temperature ranges from 40 to 65° C. and the optimal temperature is 60° C.

(v) Temperature Stability

It is stable at 40° C. for 10 minutes and remains at 90% or more even at 50° C. for 10 minutes.

(vi) Effect of a Chelating Agent

Its activity is hardly inhibited even if it coexists with EDTA or EGTA, which is a chelating agent, during the measurement of its activity.

(vii) Effect of a Metal Ion

About 30% of the activity is inhibited by 1 mM cobalt ion.

(viii) Molecular Weight by the SDS-PAGE Method

It is about 43,000.

As the DNA to be a subject of the present invention, a DNA encoding a protein comprising the amino acid sequence represented by SEQ ID NO:2, a DNA encoding a protein comprising an amino acid sequence in which one or several amino acids have been deleted, replaced, or added in the amino acid sequence represented by SEQ ID NO:2 and having an L-rhamnose isomerase activity, a DNA comprising the nucleotide sequence represented by SEQ ID NO:1 or a complementary sequence thereof or a part or the whole of any of these sequences and a DNA hybridizing to such a DNA under stringent conditions and encoding a protein having an L-rhamnose isomerase activity can be preferably exemplified.

Such a DNA can be prepared by a known method from a gene library based on the information of its DNA sequence or the like. In addition, by using the nucleotide sequence represented by SEQ ID NO: 1 or a complementary sequence thereof or a part or the whole of any of these sequences as a probe, hybridization to a DNA library derived from a variety of cells is carried out under stringent conditions, and a DNA hybridizing to the probe is isolated, whereby a DNA encoding a protein having an L-rhamnose isomerase activity can also be obtained. As the hybridization conditions for obtaining such a DNA, for example, hybridization at 42° C. and a washing treatment at 42° C. with a buffer containing 1×SSC and 0.1% SDS can be exemplified, and hybridization at 65° C. and a washing treatment at 65° C. with a buffer containing 0.1×SSC and 0.1% SDS can be preferably exemplified. Incidentally, as a factor that affects the stringency of hybridization, there are various factors other than the above-mentioned temperature condition, and it is possible to realize a stringency equivalent to the stringency of hybridization illustrated above by appropriately combining various factors.

The fusion protein of the present invention may be any as long as it is the one in which the above-mentioned protein of the present invention binds to a protein translation codon. As for the protein translation codon, there is no particular restriction as long as it is a conventionally known protein translation codon. Such a fusion protein can be prepared by a usual method, and is useful also as a reagent for research in the art.

In addition, the present invention relates to a host cell containing an expression system that can express the above-mentioned protein of the present invention. Introduction of a gene encoding such a protein of the present invention into a host cell can be carried out by a method described in many standard laboratory manuals such as Davis et al. (BASIC METHODS IN MOLECULAR BIOLOGY, 1986) and Sambrook et al (MOLECULAR CLONING: A LABORATORY MANUAL, 2nd Ed., Cold Spring Harbor Laboratory Press, Cold Spring Harbor, N.Y., 1989). As the host cell, bacterial prokaryotic cells such as *E. coli, Streptomyces, Bacillus subtilis, Streptococcus* and *Staphylococcus,* and other cells can be exemplified.

In addition, the expression system may be any expression system as long as it can express the above-mentioned protein of the present invention in a host cell. Examples of the expression system may include expression systems derived from chromosome, episome and virus, for example, vectors derived from bacterial plasmid, yeast plasmid, papovavirus such as SV40, vaccinia virus, adenovirus, chicken pox virus, pseudorabies virus, or retrovirus, vectors derived from bacteriophage, transposon, and the combination of these, for example, vectors derived from genetic factors of plasmid and of bacteriophage such as cosmid or phagemid. These expression systems may contain a regulatory sequence that not only causes expression but also regulates expression.

The protein of the present invention obtained by culturing a host cell that contains the above-mentioned expression system can be used in the production of D-allose. In addition, for collecting the protein of the present invention from the cell culture and purifying the protein, a known method including ammonium sulfate or ethanol precipitation, acid extraction, anion or cation exchange chromatography, phosphocellulose chromatography, hydrophobic interaction chromatography, affinity chromatography, hydroxyapatite chromatography, and lectin chromatography, preferably high-speed liquid chromatography can be used.

A rare sugar can be defined as a monosaccharide (an aldose, a ketose and a sugar alcohol) that rarely exists in nature, however, this definition is unclear because it is not based on the structure or properties of sugar. That is, it is because the definition of the amount in which, for example, a sugar whose existing amount is a predetermined amount or lower is referred to as a rare sugar has not been given. However, as an aldose that generally exists in a large amount in nature, there are 6 types, namely, D-glucose, D-galactose, D-mannose, D-ribose, D-xylose and D-arabinose, and the other aldoses are defined as a rare sugar. As a ketose, D-fructose exists, and the other ketoses can be referred to as a rare sugar. In addition, a sugar alcohol can be produced by reducing a monosaccharide, however, D-sorbitol exists in a relatively large amount in nature, and the others exist in a small amount, therefore, these can be a rare sugar.

It has been difficult to do obtain a rare sugar so far, however, a process for producing a rare sugar from a monosaccharide that exists in a large amount in nature is being developed, and it can be produced by utilizing the technique.

Hereunder, a correlation diagram of Izumoring will be explained.

A correlation diagram in which all the monosaccharides having 4 to 6 carbon atoms are linked together based on their production processes and molecular structures (D-form and L-form) shown in FIG. 1 is the overall diagram of Izumoring. That is, what one can understand from FIG. 1 is that monosaccharides having 4, 5 and 6 carbon atoms are all linked together. In the overall diagram, the members in Izumoring C6 are linked together, the members in Izumoring C5 are linked together, the members in Izumoring C4 are linked together, and Izumorings C4, C5 and C6 are all linked together. This concept is important. In order to reduce the number of carbon atoms, a fermentation method is mainly used. It is characterized by being a big correlation diagram in which all the monosaccharides having different number of carbon atoms are linked together. In addition, it can also be understood that a monosaccharide does not have a utility value.

In Izumoring of the monosaccharides having 6 carbon atoms (hexoses), as shown in the lower portion of FIG. 1 and FIG. 5, there are, in total, 34 types of monosaccharides having 6 carbon atoms (hexoses) including 16 aldoses, 8 ketoses and 10 sugar alcohols. It is known by the studies including the studies by the present inventors that these sugars can be converted by an oxidoreductase reaction, an aldose isomerization reaction or an aldose reductase reaction. However, the upper group, the middle group and the lower group were not linked together by an enzymatic reaction in the conventional studies. In other words, though D-glucose (glucose) or D-fructose belonging to the upper group is a sugar that exists in a large amount in nature and is inexpensive, a rare sugar could not be synthesized from such a sugar. However, in the process of the study by the present inventors, an enzyme that links these was found. D-sorbose was completely unexpectedly found in a culture solution of a bacterium having an enzyme that synthesizes D-tagatose from galactitol, which was the beginning of the finding of the enzyme. From the results of investigating the cause, it was found that this bacterium produces an enzyme called D-tagatose-3-epimerase (DTE). As shown in the lower portion of FIG. 1 and FIG. 6, it is understood that this DTE is an enzyme that connects between D-tagatose and D-sorbose which was disconnected so far.

Further surprisingly, it was found that this DTE is an enzyme that epimerizes all ketoses at the C-3 position, and is a unique enzyme having an extremely broad substrate specificity so as to act on D-fructose and D-psicose, L-sorbose and L-tagatose, D-tagatose and D-sorbose, L-psicose and L-fructose, which could not be synthetically connected so far. Because of the finding of this DTE, all the monosaccharides are linked together in a ring, and the knowledge structuring of monosaccharides is completed, which was named Izumoring.

When taking a close look at FIG. 5, it is found that there are L-forms at the left side, D-forms at the right side and DL-forms in the middle, and further L-forms and D-forms are symmetric with respect to the central point (asterisk) of the ring. For example, D-glucose and L-glucose are symmetric with respect to the central point. Further, the worth of Izumoring is that it becomes a plan diagram for production of all monosaccharides. In the previous example, if L-glucose is intended to be produced from D-glucose as a starting material, it is indicated that D-glucose is isomerized, epimerized, reduced, oxidized, epimerized and isomerized, whereby L-glucose can be produced.

By using Izumoring of monosaccharides having 6 carbon atoms (hexoses), the correlation between sugars that exist in a large amount in nature and rare sugars that exist only in a small amount is shown. D-glucose, D-fructose, D-mannose and D-galactose that can be produced from lactose in milk exist in a large amount in nature, and the others are classified into a rare sugar that exists only in a small amount. Because of the finding of DTE, D-fructose and D-psicose are produced from D-glucose, and further it becomes possible to produce D-allose, allitol and D-talitol.

When the meanings of Izumoring of monosaccharides having 6 carbon atoms (hexoses) are summarized, they include as follows. Based on the production process and molecular structure (D-form and L-form), all the monosaccharides are put in order structurally (knowledge structuring), whereby the overall picture of monosaccharides can be understood; an effective and efficient approach for study can be selected; the optimum production pathway can be designed; and a missing portion can be predicted.

Figure 6:
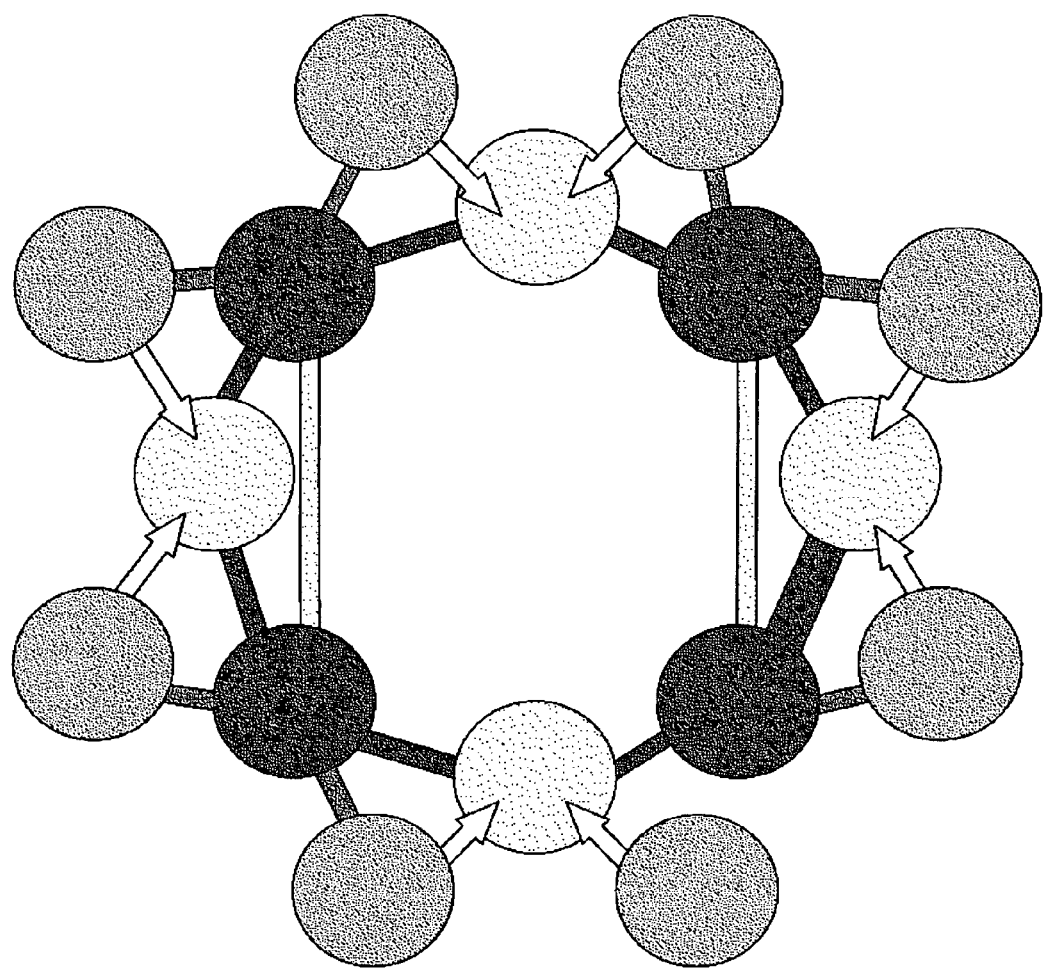
FIG. 6 is an illustration of Izumoring C5 at the middle portion of FIG. 1.

Izumoring of monosaccharides having 5 carbon atoms (pentoses) is a ring smaller than Izumoring of carbon number 6 as shown in the middle portion of FIG. 1 and FIG. 6. However, it includes all, namely, 8 aldoses, 4 ketoses and 4 sugar alcohols, in the same manner as Izumoring of C6, and all are linked together by an enzymatic reaction. The different point is that they can be all linked together in a ring by only an oxidation-reduction reaction and an isomerization reaction. On the other hand, it can be understood that by using DTE, a more efficient production pathway can be designed.

With regard to the characteristic of Izumoring of carbon number 5, as particularly clear from FIG. 6, a major characteristic is that all the monosaccharides are placed bilaterally symmetrically while in Izumoring of carbon number 6, all the monosaccharides are placed point symmetrically. Since these pentoses are linked together by an enzymatic reaction, in exactly the same manner as the case of Izumoring of carbon number 6, it has the meanings that all the pentoses are put in order structurally (knowledge structuring), whereby the overall picture can be understood, an effective and efficient approach for study can be selected, the optimum production pathway can be designed, and a missing portion can be predicted.

Izumoring of monosaccharides having 4 carbon atoms (tetroses) has a characteristic that a ring is not completed due to the structural property of tetrose as shown in the upper portion of FIG. 1. It has a structure of the upper half of Izumoring of carbon number 5. In the case of this ring, they are linked together by an oxidation-reduction reaction and an isomerization reaction in the same manner as the cases of carbon number 5 and 6. Since DTE does not react with a ketose having 4 carbon atoms, a reaction between ketoses does not exist at present. However, the existence of a novel epimerase is predicted, and this study is being performed at the moment.

The overall layout is bilaterally symmetric in the same manner as that of the carbon number 5, including all, namely, 4 aldoses, 2 ketoses and 3 sugar alcohols. That is, it has the same meanings as those of Izumorings of carbon number 5 and 6.

D-glucose in Izumoring C6 is linked to D-arabitol in Izumoring C5 and erythritol in Izumoring C4. These lines indicate that D-arabitol and erythritol can be produced from D-glucose by a fermentation method. That is, Izumoring C6, Izumoring C5 and Izumoring C4 are linked together. This linkage is a reaction of decreasing the carbon number by a mainly fermentation method, and it is possible to link Izumoring C6 to Izumoring C5 or C4 by a fermentation method other than these two conversion reactions into D-arabitol and erythritol. For example, it is possible to produce D-ribose from D-glucose.

As described above, by the three Izumorings, all the monosaccharides having 4, 5 and 6 carbon atoms (aldoses, ketoses and sugar alcohols) are linked together, therefore the location of each monosaccharide in the overall monosaccharides can be clearly identified.

It can be clearly identified that the most famous xylitol can be easily produced by reducing D-xylose that can be produced from wood material of an unused resource.

In the case where a large amount of a specific monosaccharide is obtained by a biological reaction, it is possible to easily find the possibility of conversion into a new monosaccharide using it as a raw material. That is, since the location of all the monosaccharides as a raw material can be surely identified from this overall picture, a useful application method can be designed. In particular, an application method can be easily deduced when a monosaccharide is obtained from a waste material or a by-product.

In the present invention, an isomerase that acts on many types of rare aldoses and is most efficient for producing many types of rare ketoses as described above in the rare sugar strategy of Izumoring (FIG. 1) can be obtained, whereby it becomes possible to establish a reaction for producing many types of rare sugars. That is, it becomes possible to apply a further revealed novel catalytic function to the production of a rare sugar using the overall diagram of Izumoring, and further to contribute to the search for a physiological activity of a rare sugar.

Figure 8:
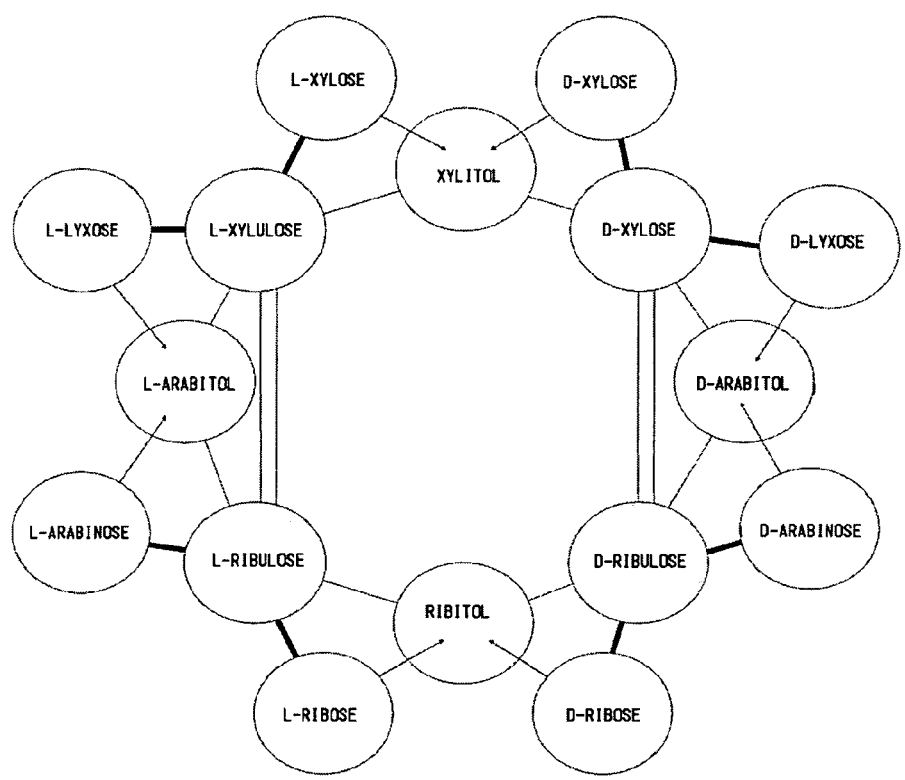
FIG. 8 shows isomerization reactions of pentoses catalyzed by L-rhamnose isomerase shown by using Izumoring. The bold black lines indicate the isomerization reactions which were identified to be catalyzed. All the isomerization reactions were confirmed.

As is clear from Izumorings in FIG. 7, FIG. 8 and FIG. 9, it is indicated how effective putting isomerization reactions in order using Izumoring is as a means for understanding the overall view. Further, it can be understood that L-rhamnose isomerase acts on many types of monosaccharides as a substrate.

In other words, though the activities vary in degree, the isomerization reactions which were confirmed to be catalyzed by L-rhamnose isomerase are represented by the bold lines in FIG. 7. On the other hand, it can be plainly understood that there are 4 types of reactions represented by the bold dotted lines, in which the isomerization reaction could not be confirmed.

In addition, as shown in FIG. 8 and FIG. 9, though the activities also vary in degree, it is shown that it has all the isomerization activities for pentoses and tetroses.

As described above, by utilizing Izumoring, a reaction catalyzed by L-rhamnose isomerase can be clearly indicated, and at the same time, the one in which a reaction cannot be confirmed can be clearly recognized.

Though it is necessary to investigate a detail reaction mechanism for a variety of isomerization activities that were newly confirmed, for example, the mechanism that the results of the reaction from an aldose and of the reaction from a ketose are somewhat different, etc., as shown in FIG. 7, FIG. 8 and FIG. 9, it was found that there is a possibility that the isomerization activities can be applied to the production of so many types of rare sugars.

The detail of the invention of this application will be described with reference to Examples. The invention of this application is by no means limited to these Examples.

EXAMPLE 1

As one method of producing a large amount of L-rhamnose, an increase of production by a genetic engineering technique is considered. Therefore, a gene encoding the present enzyme is cloned by a conventional method, and the gene sequence and the amino acid sequence were determined. The results are as follows.

[Sequencing]

L-rhamnose isomerase gene derived from *Pseudomonas stutzerii* LL172 is a novel L-rhamnose isomerase gene that comprises an open reading frame of 1,290 bp and encodes 430 amino acid residues as shown in Sequence Listing 1 and FIG. 2. The molecular weight calculated from the amino acid sequence in Sequence Listing 2 is 46,946, which was little bit higher than the authentic enzyme molecular weight of about 43,000.

When the present gene was recombinantly expressed in *E. coli,* the present enzyme was actively expressed and the molecular weight thereof corresponds to about 43,000.

The results of expression of enzyme in the case of the experiment of insertion into *E. coli* are as follows.

Accordingly, the gene sequence shown in Sequence Listing 1 and FIG. 2 were confirmed to be the L-rhamnose isomerase gene.

[Characteristic of the Present Gene Sequence]

The structure of the L-rhamnose isomerase gene has been already analyzed with the gene derived from *E. coli* and *Bacillus subtilis.* However, the amino acid sequence homology with L-rhamnose isomerase derived from *Pseudomonas stutzerii* LL172 strain is low (20% or lower) as shown in FIG. 3, and also the catalytic sites do not correspond, therefore, it was determined that they are not identical enzymes.

That is, it was an enzyme having an entirely new gene sequence different from L-rhamnose isomerase published so far.

When the homology of the amino acid sequence was analyzed using database, as shown in FIG. 4, it shows a high homology of about 40% with an unidentified putative isomerase. However, the results were obtained by sequencing the genes derived from these strains by a genome project, and the identification has not been made as an enzyme.

From the above results, it could be determined that the L-rhamnose isomerase gene derived from the present strain is a gene encoding a novel enzyme.

[Use]

Since the gene sequence was specified, a variety of experiments by a molecular biological technique utilizing this gene sequence can be performed.

For example, it is possible to perform mass production by transforming *E. coli* with this gene. Alternatively, for example, by further ligating any new gene to this gene, it is possible to produce an enzyme having a new property.

EXAMPLE 2

<DNA Encoding L-Rhamnose Isomerase>

1. Purification of L-Rhamnose Isomerase and Partial Amino Acid Sequencing

*Pseudomonas stutzerii* LL172 is cultured at 30° C. for 2 days in a tryptic soy broth medium, which is subjected to polyethylene glycol fractionation and anion exchange chromatography for purification. Then, electrophoresis is carried out and the molecular weight and purity are confirmed. The molecular weight is obtained as a single band at around 42,000. The enzyme was partially degraded with cyanogen bromide, and the N-terminus and 4 partial amino acids were sequenced.

2. Probe Synthesis and Chromosome Mapping

After the cultivation with the above-mentioned medium, chromosomal DNA is extracted using CTAB according to the standard method. A primer mix is synthesized based on the partial amino acid sequences, and a specifically amplified PCR product is obtained by performing PCR twice changing the combination of primers, which is used as a probe. By using the probe, Southern hybridization was carried out, and the location of L-rhamnose isomerase gene on the chromosome was determined.

3. Genomic Library Screening

Since it was found that the gene was contained in an about 4.6-kb fragment digested with restriction enzymes ApaI and SacI by chromosome mapping, the fragment was ligated into a cloning vector pBluescript II SK(+) to construct a genomic library, and screening was carried out using the probe.

4. L-Rhamnose Isomerase Gene Analysis

L-rhamnose isomerase gene is a novel L-rhamnose isomerase gene that comprises an open reading frame of 1,290 bp and encodes 430 amino acid residues (Sequence Listing 2) as shown in Sequence Listing land FIG. 2. The molecular weight calculated from the amino acid sequence is 46,946, which is little bit higher than the molecular weight (about 42,000) of the enzyme of the original strain subjected to modification at the C-terminal side. The structure of the L-rhamnose isomerase gene has been already analyzed with the gene derived from *E. coli* and *Bacillus subtilis.* However, the amino acid sequence homology with L-rhamnose isomerase derived from the present strain is low (20% or lower) as shown in FIG. 3, and also the catalytic sites do not correspond, therefore, it was determined that they are not identical enzymes. The five positions out of 9 positions of consensus amino acid residues of the isomerase conserved in L-rhamnose isomerase derived from *E. coli* and xylose isomerase derived from mycobacteria are conserved, however, a Mn-binding site or a substrate-binding site are not conserved. When the homology of the amino acid sequence was analyzed using database, as shown in FIG. 4, it shows a high homology of about 40% with an unidentified putative isomerase. However, the results were obtained by sequencing the genes derived from these strains by a genome project, and the identification has not been made as an enzyme.

From the above results, it was determined that the L-rhamnose isomerase gene derived from the present strain is a gene encoding a novel enzyme.

5. Active Expression of Recombinant L-Rhamnose Isomerase

A primer was designed in such a manner that the translation initiation codon of L-rhamnose isomerase corresponds to the translation initiation codon of a high expression vector pQE60, and the L-rhamnose isomerase gene amplified by PCR was integrated into pQE60, and then, *E. coli* JM109 was transformed with the vector, whereby a recombinant *E. coli* was constructed. When the recombinant *E. coli* was cultured overnight at 37° C. in a standard medium, it actively expressed L-rhamnose isomerase. The N-terminal amino acid sequence, the molecular weight and the respective enzymological properties correspond to those of the enzyme derived from the original strain, and the production amount of enzyme was increased by 10-fold or more, whereby high expression became possible.

EXAMPLE 3

Production of D-lyxose, which is a rare sugar, from D-glucose was carried out. By using yeast *Candida famata* R28, D-arabitol was produced from D-glucose with a yield of 50%. This reaction was carried out by a fermentation method. The produced D-arabitol was converted into D-xylulose by an acetic acid bacterium *Acetobacter aceti* IFO 3281 with a yield of almost 100%. This could be isomerized to D-lyxose by using L-ribose isomerase. The product was purified and crystallized by ion exchange chromatography and the like, and it was confirmed to be D-lyxose by an instrumental analysis.

That is, it is possible to produce a rare sugar, D-lyxose, by conversion into D-lyxol which has one carbon atom less by a fermentation method using D-glucose as a raw material, and by subjecting it to an oxidation reaction and an isomerization reaction (Journal of Bioscience and Bioengineering, Vol. 88, 676, 1999).

EXAMPLE 4

Production of a rare sugar, L-erythrose, was carried out from erythritol, in which erythritol was produced from D-glucose as a raw material by a fermentation method. By using *Gluconobacter frateurii* IFO 3254, erythritol was oxidized into L-erythrulose. The product was obtained with a yield of almost 100% by this reaction. L-erythrulose was separated from the reaction solution, and a rare sugar, L-erythrose, could be produced from L-erythrulose as a raw material by allowing L-ribose isomerase to act on. From 10 g of erythritol, 1.7 g of L-erythrose could be produced (Journal of Bioscience and Bioengineering, Vol. 92, 237, 2001).

That is, it is possible to produce a rare sugar, L-erythrose, by producing erythritol which has two carbon atoms less using D-glucose as a starting material by a fermentation method, and by subjecting erythritol as a raw material to an oxidation reaction and an isomerization reaction.

EXAMPLE 5

It was designed that 6 His residues were ligated to the C-terminus of the gene encoding L-rhamnose isomerase derived from *Pseudomonas stutzerii* LL172 of Example 2, and *E. coli* was transformed with the gene. This His-ligated L-rhamnose isomerase was expressed in a large amount, and a pure enzyme was produced in a large amount by affinity chromatography using a nickel NTA column, and then the obtained enzymes were used by immobilizing, respectively, whereby it became possible to allow the enzyme to exert a new function. Experiments were carried out using aldoses (Table 1) and ketoses (Table 2) as a substrate, and the experimental results of analyzing the sugar composition in the reaction solution after each reaction time by HPLC are shown in order. That is, Table 1 shows the product compositions after reaction when performing the reaction of L-rhamnose isomerase using a variety of aldoses as a substrate, and Table 2 shows the product compositions after reaction when performing the reaction of L-rhamnose isomerase using a variety of ketoses as a substrate.

TABLE 1

Conversion ratio of a variety of aldoses by L-rhamnose isomerase derived from *P. stutzeri*

| Substrate | Product[a] | | Conversion | Time[c] |
|---|---|---|---|---|
| (20 mg/ml) | Ketose | Aldose | ratio[b] (%) | (h) |
| L-rhamnose | L-rhamnulose | nd | 55:45 | 1 |
| D-glucose | D-fructose | D-mannose | 51:44:5 | 12 |
| L-glucose | L-fructose | L-mannose | 71:21:5 | 96 |
| L-mannose | L-fructose | L-glucose | 26:62:12 | 96 |
| D-mannose | D-fructose | D-glucose | 90:4:6 | 96 |
| D-galactose | D-tagatose | nd | 92:8 | 144 |
| L-galactose | L-tagatose | L-talose | 50:48:2 | 24 |
| D-gulose | D-sorbose | nd | 10:90: | 8 |
| D-altrose | D-psicose | D-allose | 8:70:22 | 24 |
| D-xylose | D-xylulose | D-lyxose | 58:40:2 | 48 |
| L-xylose | L-xylulose | L-lyxose | 61:35:4 | 48 |
| D-lyxose | D-xylulose | D-xylose | 40:4:56 | 48 |

TABLE 1-continued

Conversion ratio of a variety of aldoses by L-rhamnose isomerase derived from *P. stutzeri*

| Substrate | Product[a] | | Conversion | Time[c] |
|---|---|---|---|---|
| (20 mg/ml) | Ketose | Aldose | ratio[b] (%) | (h) |
| L-lyxose | L-xylulose | L-xylose | 50:3:37 | 48 |
| D-arabinose | D-ribulose | D-ribose | 74:10:16 | 72 |
| L-arabinose | L-ribulose | nd | 94:4 | 72 |
| D-ribose | D-ribulose | D-arabinose | 16:14:70 | 96 |
| L-ribose | L-ribulose | L-arabinose | 45:47:8 | 96 |
| D-erythrose | D-erythrulose | D-threose | 12:78:10 | 8 |
| L-erythrose | L-erythrulose | L-threose | 69:25:6 | 8 |
| D-threose | D-erythrulose | D-erythrose | 26:61:13 | 8 |
| L-threose | L-erythrulose | L-erythrose | 33:63:4 | 8 |

[a]in all the cases, a ketose was produced first.
[b]Ratio = (substrate:ketose:aldose)
[c]The time when the highest conversion ratio was obtained is shown.
nd: not detected

TABLE 2

Conversion ratio of a variety of ketoses by L-rhamnose isomerase derived from *P. stutzeri*

| Substrate | Product | | Conversion | Time[c] |
|---|---|---|---|---|
| (20 mg/ml) | Aldose I[a] | Aldose II | ratio[b] (%) | (h) |
| D-fructose | D-mannose | D-glucose | 46:4:50 | 12 |
| L-fructose | L-mannose | L-glucose | 75:14:11 | 96 |
| L-tagatose | L-galactose | L-talose | 48:45:7 | 72 |
| D-tagatose | D-galactose | nd | 89:11 | 96 |
| L-sorbose | L-gulose | nd | 94:6 | 96 |
| D-sorbose | D-gulose | nd | 90:10 | 96 |
| D-psicose | D-allose | D-altrose | 70:22:8 | 96 |
| L-psicose | nd | L-altrose | 94:6 | 96 |

[a]in all the cases, initially observed aldose
[b]Ratio = (substrate:aldose:aldose)
[c]The time when the highest conversion ratio was obtained is shown.
nd: not detected

EXAMPLE 6

(Km and Vmax of Enzyme for Each Substrate)

An enzyme was obtained with the same conditions as those of Example 5. The measurement of Km and Vmax was carried out using the enzyme without immobilizing. The results are shown in Table 3 in order. That is, Table 3 shows the results of measuring Km and Vmax of the purified L-rhamnose isomerase for a variety of substrates.

TABLE 3

Km and Vmax of L-rhamnose isomerase derived from *P. stutzeri* for a variety of aldoses

| Substrate | Km (mM) | Vmax (U/mg) |
|---|---|---|
| L-rhamnose | 11.9 | 238 |
| L-mannose | 55.5 | 138.9 |
| D-ribose | 38.5 | 21.4 |
| L-lyxose | 61.7 | 123.4 |
| D-xylose | 250 | 1.1 |
| D-glucose | 564 | 0.01 |
| D-allose | 42 | 6.76 |
| D-altrose | 71 | 0.01 |
| D-arabinose | 127.4 | 0.067 |

TABLE 3-continued

Km and Vmax of L-rhamnose isomerase derived
from *P. stutzeri* for a variety of aldoses

| Substrate | Km (mM) | Vmax (U/mg) |
|---|---|---|
| L-arabinose | 2.35 | 0.061 |
| L-xylose | 203 | 0.0065 |

EXAMPLE 7

(Detail Description of Microorganism Used in Examples 5 and 6)

*E. coli* JM109 into which L-rhamnose isomerase gene with His-tag at the C-terminus had been introduced was used.

(Culture Medium Composition and Culture Conditions)

*E. coli* JM109 was inoculated into a culture medium containing 3.5% polypepton, 2.0% yeast extract and 0.5% NaCl (pH 7.0), and cultured at 28° C. for 12 hours, and then IPTG (Isopropyl-β-D-thiogalactopyranoside) was added at a final concentration of 1 mM. Then, cultivation was continued for 4 hours, and the cells were harvested by centrifugation.

(Extraction of Enzyme, Purification of Enzyme, and Purification and Immobilization of Enzyme)

The cells were washed twice with 0.05 M sodium phosphate buffer (pH 7.0). The washed cells were ground with alumina powder and subjected to centrifugation to remove insoluble substances together with alumina powder, whereby a crude enzyme solution was obtained. The obtained crude enzyme solution was subjected to affinity chromatography using an Ni-NTA column to purify the enzyme, whereby a pure enzyme was obtained. After the enzyme was dialyzed against ultrapure water, lyophilization was carried out, whereby pure powder enzyme was obtained. By allowing 20 mg of the enzyme to be adsorbed on 1 g of Chitopearl resin, immobilized enzyme was prepared.

(Enzymatic Reaction Conditions Using Various Substrates)

A reaction was carried out at 42° C. with a composition of enzymatic reaction solution containing 3 g of the above-mentioned immobilized enzyme, 3.0 mL of 0.05 M glycine-NaOH buffer (pH 9.0), 3.0 μL of 1 M $MnCl_2$ and 60 mg of any of various substrates (final concentration of 20 mg/mL)

INDUSTRIAL APPLICABILITY

1. It becomes possible to produce L-rhamnose isomerase in a large amount by a genetic engineering technique, and a mass production method of a variety of rare sugars containing D-allose using the present enzyme can be established.

L-rhamnose isomerase was isolated from a variety of microorganisms and the gene sequence encoding it has been also reported. In the present invention, when the gene sequence encoding L-rhamnose isomerase from a bacterium (*Pseudomonas stutzeri*) isolated from the soil was determined, it was found that the gene sequence does not have homology with the gene sequences which had been reported so far, and it is a novel gene on a gene basis as well as a protein basis.

By utilizing this sequence, this gene sequence can be applied to the production of a rare sugar by using genetic engineering, or to the use using a variety of genetic engineering techniques.

2. With regard to a conventional effective utilization of unused resources, particularly plant biomass (e.g., wood, a variety of unused plant resources and the like), a major goal was to hydrolyze it into glucose and to convert the glucose into an alcohol. However, even if it was converted into an alcohol, since its added value is low, it was unreasonable to put it into practical use. Though the present invention is the same as conventional methods up to the point of conversion into a monosaccharide such as glucose, a characteristic of the present invention is conversion into a rare sugar by a variety of biological reactions instead of alcohol fermentation by yeast after the conversion into a monosaccharide. In this way, a process that can produce a rare sugar having a high added value from an alcohol having a low added value can be provided.

3. By using a polysaccharide (which exists unlimitedly in unused plant resources) as a raw material, and a method of incompletely degrading it or another method, an oligosaccharide can be produced. Its application is also being developed as a value-added product having a functionality. However, when it is degraded to a minimum unit, namely a monosaccharide, it was considered that there was no new development. The breakthrough is that a production strategy aiming at conversion from one monosaccharide (rare sugar) to a new monosaccharide (rare sugar) continuously could be established, which is considered to have significant meanings. When a polysaccharide is degraded, it becomes a monosaccharide, and using it as a raw material, a monosaccharide (rare sugar) is produced continuously, which is an innovative idea. A polysaccharide is an upstream raw material, therefore, it is degraded to produce a monosaccharide, and it is used as a raw material. The basic strategy is that whether the raw material is wood (cellulose) or starch, or whatever, or no matter how different polysaccharide is, when it is degraded to a monosaccharide, it becomes the same substance.

4. What one can understand from FIG. 1 is that monosaccharides having 4, 5 and 6 carbon atoms are all linked together. The members in Izumoring C6 are linked together and the members in Izumorings C4, C5 and C6 are all linked together. This concept is important. In order to reduce the number of carbon atoms, a fermentation method is mainly used. It is also characterized by being a big correlation diagram in which all the monosaccharides having different number of carbon atoms are linked together. Even if any waste material or carbohydrate byproduct is obtained, its utilization method can be deduced from this diagram. In addition, it can also be understood that a material does not have a utility value.

5. In a study plan for monosaccharides, there was no idea of viewing all the monosaccharides having different number of carbon atoms comprehensively (see FIG. 10). Individual reactions were carried out according to the individual objectives. By comprehensively correlating the studies, which had been advanced for the individual objectives, a direction of connecting mutual techniques can be found. For example, as long as a material treated as a nuisance such as a waste material or a byproduct is a monosaccharide, it becomes possible to determine the value for any of such a material, and to tell what it is used for as a raw material immediately. In this way, a new technical concept of viewing the overall monosaccharides as a diagram or a system can be presented.

6. This technical concept of the present invention leads to a method of reevaluating a monosaccharide or evaluating the value of a monosaccharide. By taking account of the overall monosaccharides, a general idea that a monosaccharide is "a simplest organic compound in nature" is changed and leads to a system enabling to sense that it is an organic compound that is complex and moreover, gives greater chances.

7. There is an importance to enable to recognize the fact that "there is no monosaccharide other than these" or "these are all monosaccharides". In other words, it indicates that a study plan, in which by studying all so much, the overall monosaccharides can be understood, can be made clear. Knowing the limitation leads to knowing the possibility.

8. The present invention exhibits an effectiveness not only in a production field of a rare sugar, but also in a study of searching for a physiological activity possessed by a rare sugar. For example, when a physiological activity is found in a certain rare sugar, its location in the correlation diagram shown in FIG. 1 is identified. Then, comparison with the physiological activity for a rare sugar having a close structure, or examination of the physiological activity of the rare sugar in a mirror image configuration will assist us to deduce the mechanism of the physiological activity from the structure of the molecule. In addition, it is expected that it can be applied dominantly to the study of the physiological activity which was performed randomly through a trial and error process so as to proceed according to the plan based on the understanding of the overall picture of Izumoring.

9. The present invention exhibits a usefulness as a production strategy for a rare sugar and also exhibits a usefulness in a study of its use, particularly of a physiological activity. This enables the systematization of the linkage of the individual monosaccharides in the production by an enzymatic reaction from the conventional enumerative classification and individual recognition method of monosaccharides based only on their structures. Further, it is expected that all the monosaccharides can be applied a great deal to the comprehensive understanding of "structure of monosaccharide", "production process for monosaccharide" and "physiological function of monosaccharide" from the conventional simple enumerative understanding by analyzing the physiological functions of rare sugars and integrating the properties on Izumoring.

10. All the isomerization reactions including a novel catalytic reaction of L-rhamnose isomerase revealed in the present invention are shown in Izumorings of FIG. 7, FIG. 8 and FIG. 9. As is clear from the figures, it is indicated how effective putting the isomerization reactions in order by using Izumoring is as a means for understanding the overall view. Further, it can be understood that many types of the monosaccharides are used as a substrate for L-rhamnose isomerase.

That is, though the activities vary in degree, the isomerization reactions which were confirmed to be catalyzed by L-rhamnose isomerase are represented by the bold lines in FIG. 7. On the other hand, it can be plainly understood that there are 4 types of reactions represented by the bold dotted lines, in which the isomerization reaction could not be confirmed.

In addition, as shown in FIG. 8 and FIG. 9, though the activities also vary in degree, it is shown that it has all the isomerization activities for pentoses and tetroses.

11. As described above, by utilizing Izumoring, a reaction catalyzed by L-rhamnose isomerase can be clearly indicated, and at the same time, the one in which a reaction cannot be identified can be clearly recognized.

12. Though it is necessary to investigate a detail reaction mechanism for a variety of isomerization activities that were newly confirmed, for example, the mechanism that the results of the reaction from an aldose and of the reaction from a ketose are somewhat different, etc., as shown in FIG. 7, FIG. 8 and FIG. 9, it was found that there is a possibility that the isomerization activities can be applied to the production of so many rare sugars.

The invention claimed is:

1. An isolated or purified protein comprising the amino acid sequence represented by SEQ ID NO:2 and having L-rhamnose isomerise activity.

2. An isolated or purified protein comprising an amino acid sequence encoded by a DNA sequence that hybridizes with the nucleotide sequence of SEQ ID NO: 1 at stringency conditions comprising a wash with a buffer containing 0.1×SSC and 0.1% SDS at 65° C. and having L-rhamnose isomerase activity.

3. The protein according to claim 1 or 2, wherein the L-rhamnose isomerase activity is specified by the following physicochemical properties:
   (i) an action
      which catalyzes an isomerization reaction represented by any of the bold black lines in FIG. 7, FIG. 8 and FIG. 9;
   (ii) an active pH and an optimal pH
      in which the active pH ranges from 7.0 to 10.0 and the optimal pH is 9.0;
   (iii) pH stability
      in which it is stable within the pH range of 6.0 to 11.0 in the case where it is kept at 40° C. for 1 hour at various pH values;
   (iv) an active temperature and an optimal temperature
      in which the active temperature ranges from 40 to 65° C. and the optimal temperature is 60° C.;
   (v) a temperature stability
      in which it is stable at 40° C. for 10 minutes and retains at least 90% activity even at 50° C. for 10 minutes;
   (vi) an effect of a chelating agent
      in which its activity is not substantially inhibited by EDTA or EGTA;
   (vii) an effect of a metal ion
      in which about 30% of the activity is inhibited by 1 mM cobalt ion; and
   (viii) a molecular weight by the SDS-PAGE method which is about 43,000.

* * * * *

SEQUENCE LISTING

```
<160> NUMBER OF SEQ ID NOS: 2

<210> SEQ ID NO 1
<211> LENGTH: 1290
<212> TYPE: DNA
<213> ORGANISM: Pseudomonas stutzerii

<400> SEQUENCE: 1
atggctgaat tcaggatcgc tcaggatgtc gttgcgcggg aaaacgacag gcgcgcctcg      60
gcgctgaagg aagactacga ggcgctcggc gcgaatctcg cccgccgtgg cgtcgacatc     120
gaggccgtca cggccaaggt cgaaaagttc ttcgtcgccg tccctcctg gggcgtcggc      180 acgggcggca cgcgctttgc gcgcttcccc ggcaccggcg agccgcgcgg catcttcgac     240
aagctggacg actgcgccgt catccagcag ctgacacgcg ccacgcccaa tgtctcgctg     300
catattccgt gggacaaggc cgatccgaag gagctgaagg ccagggggcga cgccctcggc     360 ctcggcttcg acgcgatgaa ctccaatacc ttctccgatg cgcccggcca ggcgcattcc     420
tacaaatacg gctcgctcag ccacacggat gcggcaacgc gcgcccaggc ggtcgagcac     480
aatctggaat gcatcgagat cggcaaggcc atcggctcca aggcgctgac ggtctggatc     540
ggtgacggct ccaacttccc cggccagagt aacttcacca gggctttcga acgttatctc     600
```

-continued

```
tcggcgatgg cggagatcta caagggcctg ccggatgact ggaagctgtt ctccgagcac    660
aagatgtacg agccggcctt ctattcgacc gtcgtgcagg actggggcac gaattatctc    720
atcgcccaga cgctcggccc caaggcccag tgcctcgtcg atctcggcca tcacgcgccg    780
aacaccaata tcgagatgat cgtcgcccgg ctcatccagt tcggcaagct cggcggcttc    840
catttcaacg attccaaata cggcgacgac gacctcgatg ccggcgccat cgagccctat    900
cgcctcttcc tcgtcttcaa cgagctggtg gatgcggagg cgcgcggcgt caagggcttc    960
cacccggccc acatgatcga ccagtcgcac aacgtcaccg acccgatcga gagcctgatc   1020
aacagcgcga acgaaatccg tcgcgcctat gcgcaggccc tccttgtcga ccgcgcggcg   1080
ctttccggct accaggagga caacgacgcc ctgatggcga cggaaacgtt gaagcgcgcc   1140
taccgtaccg atgtggagcc gatcctcgcc gaggcccgcc gccgcacggg cggcgccgtc   1200
gaccccgtcg cgacctatcg ggccagcggc taccgcgcca gggtcgccgc cgagcgcccc   1260
gcctccgtcg cgggtggcgg cggcatcatc                                   1290
```

<210> SEQ ID NO 2
<211> LENGTH: 430
<212> TYPE: PRT
<213> ORGANISM: Pseudomonas stutzerii

<400> SEQUENCE: 2

```
Met Ala Glu Phe Arg Ile Ala Gln Asp Val Ala Arg Glu Asn Asp
1               5                   10                  15

Arg Arg Ala Ser Ala Leu Lys Glu Asp Tyr Glu Ala Leu Gly Ala Asn
            20                  25                  30

Leu Ala Arg Arg Gly Val Asp Ile Glu Ala Val Thr Ala Lys Val Glu
        35                  40                  45

Lys Phe Phe Val Ala Val Pro Ser Trp Gly Val Gly Thr Gly Gly Thr
    50                  55                  60

Arg Phe Ala Arg Phe Pro Gly Thr Gly Glu Pro Arg Gly Ile Phe Asp
65                  70                  75                  80

Lys Leu Asp Asp Cys Ala Val Ile Gln Gln Leu Thr Arg Ala Thr Pro
                85                  90                  95

Asn Val Ser Leu His Ile Pro Trp Asp Lys Ala Asp Pro Lys Glu Leu
            100                 105                 110

Lys Ala Arg Gly Asp Ala Leu Gly Leu Gly Phe Asp Ala Met Asn Ser
        115                 120                 125

Asn Thr Phe Ser Asp Ala Pro Gly Gln Ala His Ser Tyr Lys Tyr Gly
    130                 135                 140

Ser Leu Ser His Thr Asp Ala Ala Thr Arg Ala Gln Ala Val Glu His
145                 150                 155                 160

Asn Leu Glu Cys Ile Glu Ile Gly Lys Ala Ile Gly Ser Lys Ala Leu
                165                 170                 175

Thr Val Trp Ile Gly Asp Gly Ser Asn Phe Pro Gly Gln Ser Asn Phe
            180                 185                 190

Thr Arg Ala Phe Glu Arg Tyr Leu Ser Ala Met Ala Glu Ile Tyr Lys
        195                 200                 205

Gly Leu Pro Asp Asp Trp Lys Leu Phe Ser Glu His Lys Met Tyr Glu
    210                 215                 220

Pro Ala Phe Tyr Ser Thr Val Val Gln Asp Trp Gly Thr Asn Tyr Leu
225                 230                 235                 240

Ile Ala Gln Thr Leu Gly Pro Lys Ala Gln Cys Leu Val Asp Leu Gly
                245                 250                 255
```

```
His His Ala Pro Asn Thr Asn Ile Glu Met Ile Val Ala Arg Leu Ile
            260                 265                 270

Gln Phe Gly Lys Leu Gly Gly Phe His Phe Asn Asp Ser Lys Tyr Gly
            275                 280                 285

Asp Asp Asp Leu Asp Ala Gly Ala Ile Glu Pro Tyr Arg Leu Phe Leu
            290                 295                 300

Val Phe Asn Glu Leu Val Asp Ala Glu Ala Arg Gly Val Lys Gly Phe
305                 310                 315                 320

His Pro Ala His Met Ile Asp Gln Ser His Asn Val Thr Asp Pro Ile
                325                 330                 335

Glu Ser Leu Ile Asn Ser Ala Asn Glu Ile Arg Arg Ala Tyr Ala Gln
            340                 345                 350

Ala Leu Leu Val Asp Arg Ala Ala Leu Ser Gly Tyr Gln Glu Asp Asn
            355                 360                 365

Asp Ala Leu Met Ala Thr Glu Thr Leu Lys Arg Ala Tyr Arg Thr Asp
        370                 375                 380

Val Glu Pro Ile Leu Ala Glu Ala Arg Arg Arg Thr Gly Gly Ala Val
385                 390                 395                 400

Asp Pro Val Ala Thr Tyr Arg Ala Ser Gly Tyr Arg Ala Arg Val Ala
                405                 410                 415

Ala Glu Arg Pro Ala Ser Val Ala Gly Gly Gly Ile Ile
            420                 425                 430
```